United States Patent [19]
Frei et al.

[11] Patent Number: 5,914,013
[45] Date of Patent: *Jun. 22, 1999

[54] SELECTIVE THERMAL AND PHOTOOXIDATION OF HYDROCARBONS IN ZEOLITES BY OXYGEN

[75] Inventors: Heinz Frei, Berkeley, Calif.; Fritz Blatter, Basel, Switzerland; Hai Sun, Saint Charles, Mo.

[73] Assignee: The Regents of the University of California, Oakland, Calif.

[*] Notice: This patent is subject to a terminal disclaimer.

[21] Appl. No.: 08/874,679

[22] Filed: Jun. 13, 1997

Related U.S. Application Data

[63] Continuation-in-part of application No. 08/710,031, Sep. 11, 1996, Pat. No. 5,827,406, which is a continuation of application No. 08/382,216, Jan. 31, 1995, abandoned.

[51] Int. Cl.$^6$ .................................................. C07B 33/00
[52] U.S. Cl. .............................. 204/157.15; 204/157.6; 204/157.61; 204/158.2; 568/382; 568/383; 568/398.8; 568/399; 568/400; 568/564; 568/558; 568/577
[58] Field of Search ........................... 204/157.15, 157.6, 204/157.61, 158.2, 158.21; 210/748; 568/382, 383, 398.8, 399, 400, 564, 558, 577

[56] References Cited

PUBLICATIONS

Blatter et al., *J. A. Chem. Soc.*, 115, pp. 7501 to 7502, 1993.
Blatter et al., *J. Phys. Chem.*, 98, 13403–13407, 1994.
Blatter et al., *J. Am. Chem. Soc.*, 116, 1812–1820, 1994.
Nicholas J. Turro, Photochemistry of organic molecules in microscopic reactors, *Pure & Appl. Chem.*, vol.58, No. 9, 1219–1228, (1986).
Thomas L. Pettit, et al., Photoassisted Oxygenation of Olefins: An Exchanged Zeolite as a Heterogeneous Photosensitizer, *J. Phys. Chem.*, 90, 1353–1354, (1986).
Nicholas J. Turro, et al., Photochlorination of n–Alkanes Absorbed on Pentasil Zeolites, *J. Org. Chem.*, 53, 3731–3735, (1988).

V. Ramamurthy, et al., Photochemical and Photophysical Studies of Organic Molecules Included with Zeolites, *Acc. Chem. Res.*, 25, 299–307, (1992).
Prabir K. Dutta, et al., Intrazeolitic Photoinduced Redox Reactions between Ru(bpy)$_3^{2+}$ and Methylviologen, *J. Phys. Chem.*, 96, 9410–9416, (1992).
V. Ramamurthy, Photochemical and Photophysical Studies within Zeolites, *CHIMIA*, 46, Nr. 9, 359–376, (Sep. 1992).
Kyung Byung Yoon, Electron— and Charge— Transfer Reactions with Zeolites, *Chem. Rev.*, 93, 321–339, (1993).
Fritz Blatter, et al., Very Strong Stabilization of Alkene–O$_2$ Charge–Transfer State in Zeolite NaY: Red–Light–Induced Photooxidation of 2,3–Dimethyl–2–butene, *J. A. Chem. Soc.*, 115, 7501–7502, (1993).
Fritz Blatter, et al., Diffuse Reflectance Spectroscopy of Visible Alkene–O$_2$ Charge–Transfer Absorptions in Zeolite Y and Determination of Photooxygenation Quantum Efficiencies, *J. Phys. Chem.*, 98, 13403–13407, (1994).
Fritz Blatter, et al., Selective Photooxidation of Small Alkenes by O$_2$ with Red Light in Zeolite Y, *J. Am. Chem. Soc.*, 116, 1812–1820, (1994).
Hai Sun, et al., Selective Oxidation of Toluene to Benzaldehyde by O$_2$ with Visible Light in Barium (2+)– and Calcium (2+)– Exchanged Zeolite Y, *J. Am. Chem. Soc.*, 116, 7951–7952, (1994).
Hai Sun, et al., Cyclohexanone from Cyclohexane and O$_2$ in a Zeolite under Visible Light with Complete Selectivity, *J. Am. Chem. Soc.*, 118, 6873–6879 (1996).

*Primary Examiner*—Cecilia J. Tsang
*Assistant Examiner*—C. Delacroix-Muirheid
*Attorney, Agent, or Firm*—Hana Verny

[57] ABSTRACT

A process for selective thermal oxidation or photooxidation of hydrocarbons adsorbed onto zeolite matrices. A highly selective thermal oxidation and photooxidation of unsubstituted or alkyl substituted alkanes, alkenes, aromatics and cycloalkyls in solvent free zeolites under dark thermal conditions or under irradiation with visible light. The process oxidizes hydrocarbons almost completely selectively without substantial production of byproducts.

18 Claims, 14 Drawing Sheets

N₂ in BaY and NaY

N₂ in BaL and KL

Zeolite Y

Zeolite L

SELECTIVE THERMAL AND PHOTOOXIDATION OF HYDROCARBONS IN ZEOLITES BY OXYGEN

This is a continuation-in-part application of the patent application Ser. No. 08/710,031 filed on Sep. 11, 1996, now U.S. Pat. No. 5,527,406, which is a continuation of the U.S. application Ser. No. 08/382,216, filed Jan. 31, 1995, now abandoned.

This invention was developed under the Department of Energy Contract No. DE-AC03-76SF00098. The U.S. Government may have certain rights to this invention.

BACKGROUND OF THE INVENTION

1. Field of Invention

The current invention concerns a process for selective thermal oxidation or photooxidation of hydrocarbons adsorbed onto zeolite matrices. In particular, the invention concerns highly selective thermal oxidation and photooxidation of unsubstituted or alkyl substituted alkanes, alkenes, aromatics and cycloalkyls in solvent free zeolites under dark thermal conditions or under irradiation with visible light. The process oxidizes hydrocarbons almost completely selectively without substantial production of byproducts.

2. Background and Related Disclosures

Partial oxidation of small alkanes, alkenes, and aromatics is one of the most important processes in chemical industry. The oxidated products serve as building blocks for plastics and synthetic fibers, or as industrial intermediates in the manufacture of fine chemicals. Oxidation of low alkanes plays a central role in the use of natural gas and volatile petroleum fractions as new feedstocks for industrial chemicals. For these large scale processes, molecular oxygen is the only economically viable oxidant. For most small hydrocarbons, direct oxidations by $O_2$ are very unselective. As a result, existing methods generate large amounts of unwanted byproducts which require energy-intensive separation processes.

The main reason for the lack of selectivity is the free radical nature of the gas or liquid phase processes, the high exothermicity of the reactions, and overoxidation. Unrestricted mobility of the free radical intermediates results in indiscriminate attack on starting hydrocarbon and primary oxidation products. Overoxidation is due to the fact that, under thermal conditions in liquid or gas phase, oxygen attacks partially oxidized products more easily than the starting hydrocarbon. The lack of control gets worse as products accumulate, limiting conversion to a few percent in most practical processes.

Recent efforts towards improvement of the selectivity of hydrocarbon oxidation by $O_2$ encompass a diverse spectrum of approaches. Low alkane oxidations are mainly based on catalysis over metal and mixed metal oxides (*Appl. Catal.* 128:L165 (1995)), with some of these solids acting mainly as oxidative dehydrogenation catalysts (*Topics Catal.*, 3:277 (1996)). Mixed metal oxides were shown to play an important role in oxidation of unsaturated hydrocarbons (*Appl. Catal. A.*, 143:29 (1996)). Some solid oxides have shown to be effective oxidation catalysts under irradiation with UV light (*J. Chem. Soc. Chem. Commun.*, 2125 (1996)). Other methods, such as electrochemical methods (*J. Catal.*, 157:450 (1995)) and catalysis by transition metal complexes (*J. Am. Chem. Soc.*, 116:998 (1994)) are under investigation. Although selectivities are dramatically improved over plain autoxidation, these methods still generate substantial amounts of carbon oxides or other carbon fragmentation products, some of these being produced even at low hydrocarbon conversion. Porphyrin analogs of monooxygenase enzymes that are capable of low alkane and olefin oxidation by $O_2$ to alcohols or epoxides are described in *Metalloporphyrins in Catalytic Oxidations*, R. A. Sheldon, Ed., Marcel Dekker, New York (1994). Many porphyrin systems require sacrificial reducing agents, but some afford oxidation of even small hydrocarbons without the need of a stoichiometric reductant. These include perhalo iron porphyrins (ibid.), UV light-assisted oxidation of alkanes in the presence of metalloporphyrins (*J. Chem. Soc. Chem. Commun.*, 1487 (1991)) and epoxidation of olefins by Ru porphyrin (*J. Am. Chem. Soc.*, 107:5790 (1985)). A most recent approach is oxidation in redox molecular sieves such as metal aluminophosphates or metal silicalites (*Appl. Catal. A.*, 43:3 (1996)). Selectivities of these approaches are higher, but typically only at a few percent conversion of the hydrocarbon, a persistent problem in all existing methods using $O_2$ that is especially severe for low alkanes and alkenes.

Charge-transfer from alkane (or alkene, aromat) to oxygen can be induced by absorption of a photon by a hydrocarbon•$O_2$ collisional complex or, in principle, spontaneously in a thermal process if molecules were occluded in a highly ionic environment. Light-induced formation of hydrocarbon•$O_2$ charge-transfer states has been reported in *J. Am. Chem. Soc.*, 82:5966 (1960). Optical absorptions in the UV region originating from transition to excited charge-transfer states of alkane, alkene, or aromat•$O_2$ collisional pairs were observed in $O_2^-$ saturated hydrocarbon liquids and high-pressure $O_2$ gas phase. They appear typically as long, structureless absorption tails. Upon irradiation with UV light, photooxidation was observed and interpreted by a mechanism that features proton transfer from the hydrocarbon radial cation to $O_2^-$ as the initial step (*Tetrahedron*, 41:2215 (1985)). However, these UV light-driven gas or liquid phase oxidations resulted in a multitude of products and were therefore nonselective.

It would, therefore, be highly advantageous to provide a method or process which would selectively oxidate small hydrocarbons and which would achieve selective activation via charge-transfer between hydrocarbon and $O_2-$ in such a way as to generate the radical cation•$O_2-$ pair and also which would have some means to control the chemistry of the subsequently produced radicals and primary oxidation products.

All patents, patent applications and publications cited herein are hereby incorporated by reference.

SUMMARY

One aspect of the current invention is a process for selective thermal or photooxidation of hydrocarbons adsorbed onto zeolite matrices.

Another aspect of the current invention is a selective thermal oxidation of hydrocarbons absorbed onto zeolite matrices together with oxygen by submitting the hydrocarbons to thermal reaction of temperatures from about 20° C. to about 150° C. in darkness for about 30 minutes to several days.

Still another aspect of the current invention is a selective photooxidation of hydrocarbons absorbed onto zeolite matrices together with oxygen where the loaded zeolite is subjected to visible light at wavelength from 400–700 nm for several minutes to several days at temperatures from about −100° C. to about +80° C.

Still yet another aspect of the current invention is a selective oxidation of hydrocarbons absorbed in zeolite matrices selected from the group consisting of NaY, BaY, CaY, NaL, BaL, CaL, KL or pentasil.

BRIEF DESCRIPTION OF FIGURES

FIG. 14 are graphs showing infrared difference spectrum of the NaY pellet loaded with cyclohexane and $O_2$ before and after Argon-iron laser photolysis.

DEFINITIONS

Figure 1:
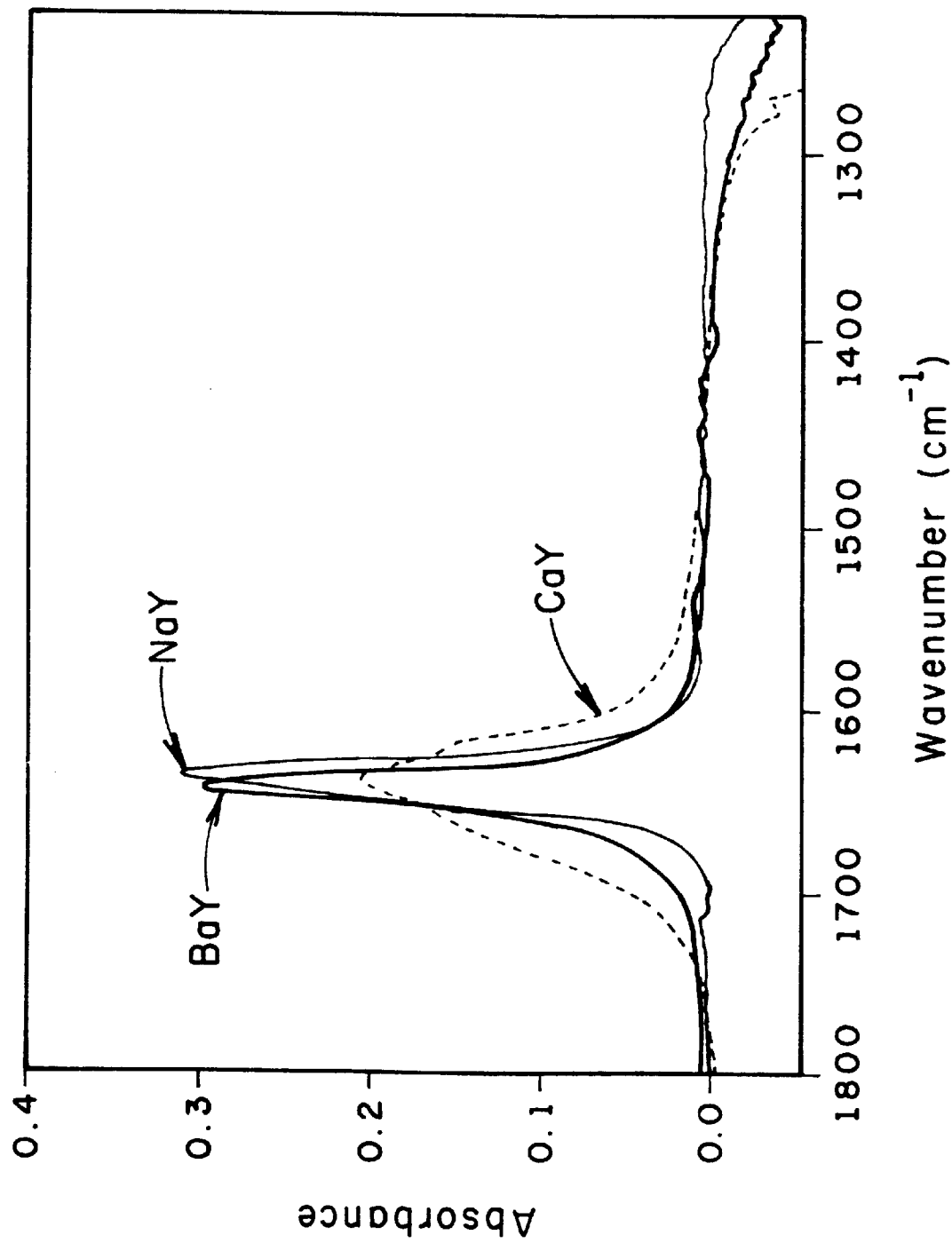
FIG. 1 is a graph showing FT-infrared spectra of NaY, BaY, and CaY pellets in the $H_2O$ bending region upon loading of water from the gas phase. Spectra are normalized to one water molecule per supercage.
Figure 2A:
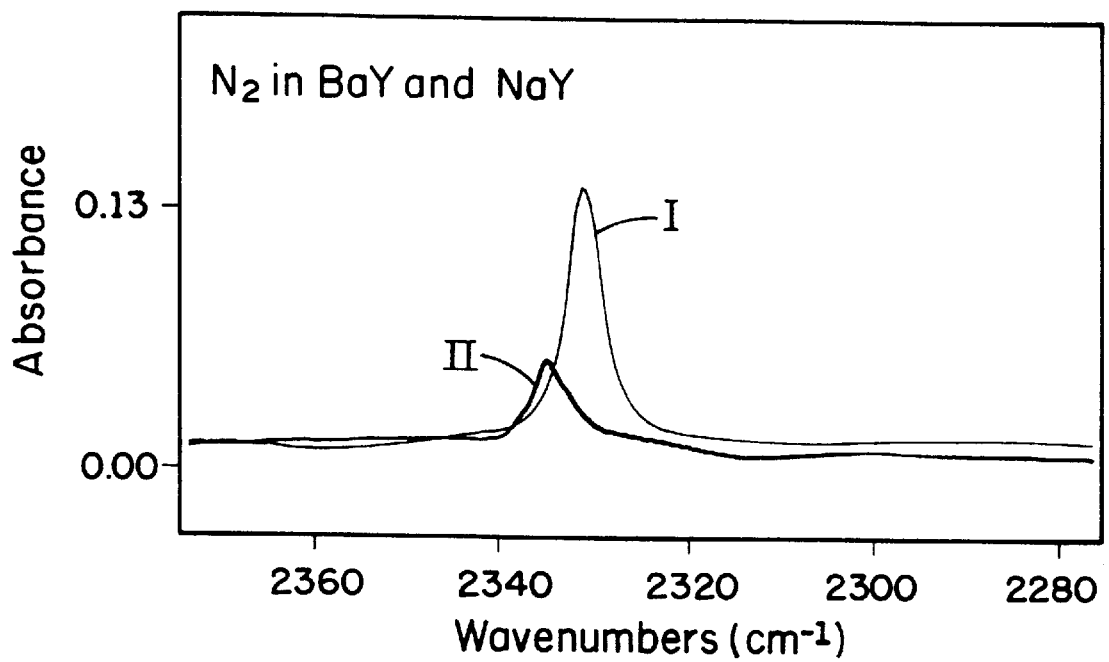
FIG. 2 is a graphical illustration of infrared absorption of $N_2$ induced by the electrostatic field in the vicinity of cations in zeolites Y (FIG. 2A) and L (FIG. 2B).
FIG. 2C shows structure of zeolite Y.
FIG. 2D shows structure of zeolite L.
Figure 2B:
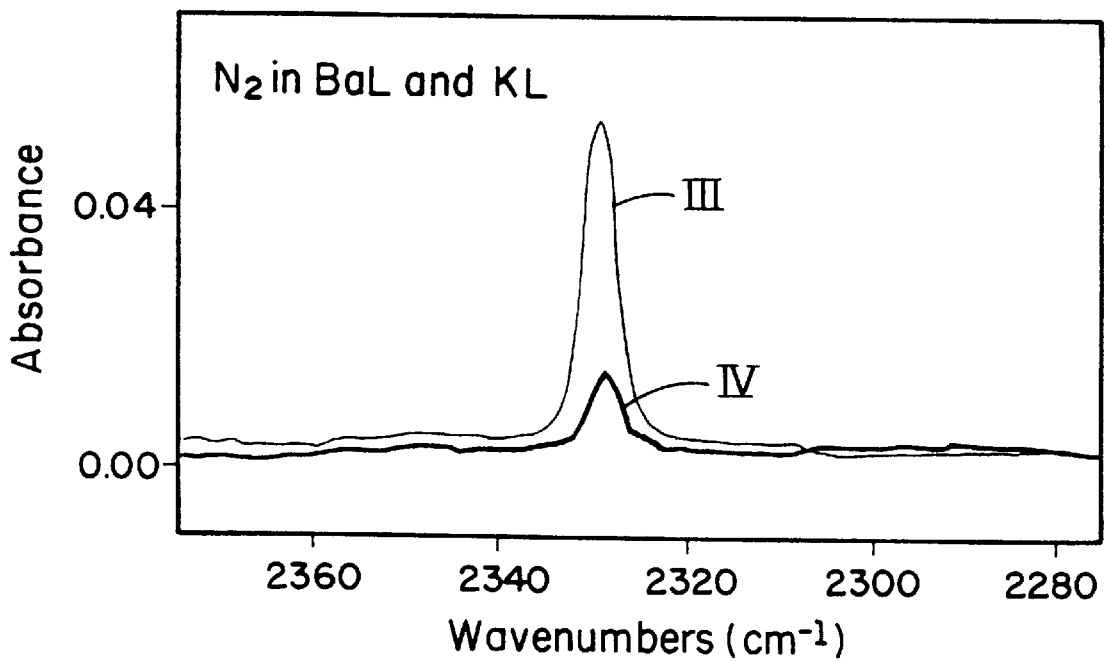
Figure 2C:
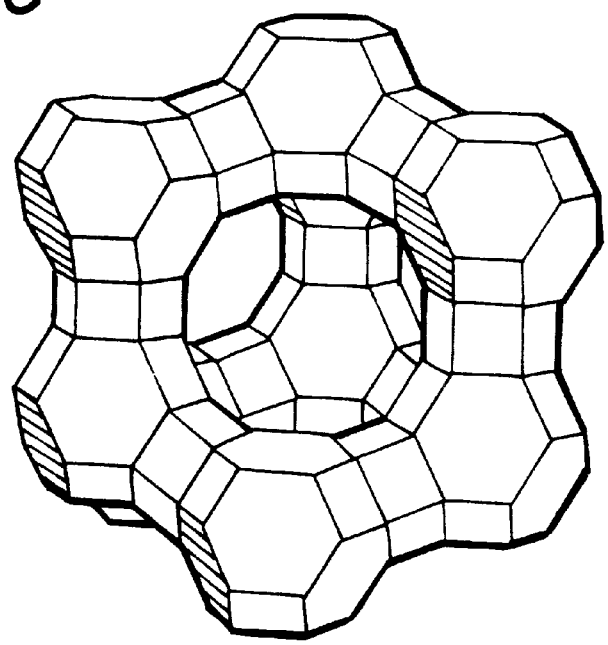
Figure 2D:
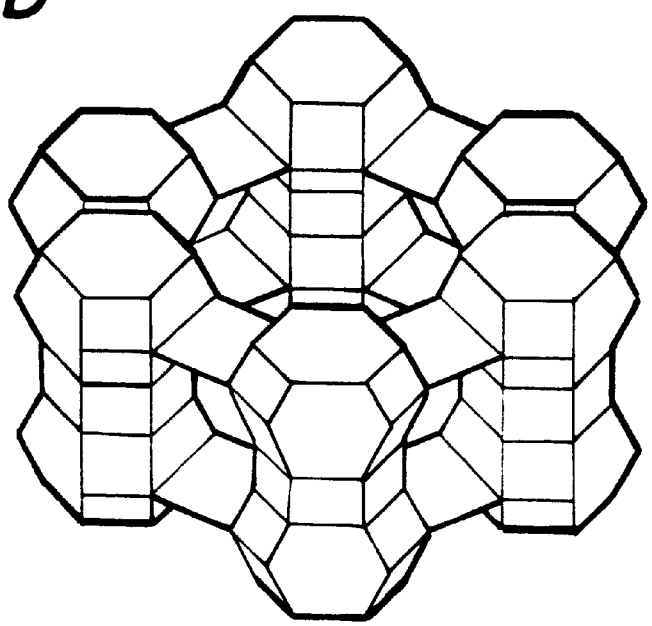

As used herein, the term:

"Zeolite" means crystalline aluminosilicates with a network of molecular-size channels or cages. Typically zeolites are hydrated aluminum and calcium, potassium, sodium or barium silicates or a synthetic resin having the properties of zeolites. Zeolite may be of type Y, L or pentasil zeolite. Zeolite Y has a ratio of silica to aluminum about 2.4. Zeolite Y, in its Na+ or $Ba^{2+}$ exchanged form, is a structure of a 3-dimensional network of 13 Å spherical cages interconnected by windows of 8 Å diameter. Zeolite L, in K or Ba form, is a 1-dimensional structure of 7 Å diameter channels.

"Supercage", "nanocage" or "channel" means the topological structure of zeolites or support materials in reference to the rather large spherical cavities which are generated by the intersection of interconnected three-dimensional networks characteristic of zeolite materials.

"Conversion" means the amount of starting hydrocarbon material which has undergone photooxidation and has reacted to form a new product or products. As such, the term is a relational one which compares the amount of unreacted starting material remaining after photooxidation with the total amount of starting material initially present to indicate the degree of completion of the photooxidation process under a certain set of conditions.

"Thermal reaction" means a spontaneous reaction that takes place in the absence of visible light at room or at higher temperatures to about 150° C.

"Photooxidation", "oxidation by visible light" or "treatment by visible light" means the exposure of hydrocarbon loaded into zeolite nanocages to energy in the visible range of the electromagnetic spectrum. Electromagnetic energy is propagated through space or through material media in the form of advancing disturbances in electric and magnetic fields which exist in space or in the media.

"Visible region", "white light" or "white visible region" of the electromagnetic spectrum is an arbitrarily defined subportion of the continuum of wavelengths which comprise electromagnetic energy, and means light which has a wavelength found in the range of 4000 to approximately 7000 angstroms (Å), or approximately 400 to approximately 700 nanometers (nm).

"Red light" means electromagnetic energy or photons having wavelengths in the range from approximately 6000 to 7000 Å or 600 to 700 nm.

"Blue light" means a light found at the opposite end of the visible spectrum and an electromagnetic energy or photons having wavelengths in the range from approximately 4000 to 4900 Å or 400 to 490 nm.

"Oxidation" or "photooxidation" when taken alone or in combination with the words "treatment", "exposure", "irradiation" or "radiation" are generally synonymous.

"Selective" or "substantially selective" means a reaction or process which results in generating the final product or products as a majority. That a particular reaction or process is "selective" means that only one primary reaction intermediate is formed at more than 95%, and that once an isolable initial product has been formed, there is no further reaction or decomposition of that product under the initial reaction conditions.

DETAILED DESCRIPTION OF THE INVENTION

The current invention concerns a selective conversion of small hydrocarbons into their oxidative derivatives by thermal oxidation or photooxidation. A process for thermal oxidation or photooxidation involves loading, as gas, a small hydrocarbon into an dehydrated alkali or alkaline earth zeolite matrix at ambient temperature and adding one to several atmospheres of oxygen gas.

Under these conditions, spontaneous partial thermal oxidation occurs at darkness at temperatures in the range from about 20° C. to about 500° C., preferably to about 150° C., after about 30 minutes to several days, preferably about 20 hours, depending on the hydrocarbon and nature of zeolite cation. Thermal oxidation produces an oxidative product, such as a ketone, as a final product.

In alternative, the hydrocarbon oxidation is induced by submitting the loaded zeolites with hydrocarbon and oxygen to irradiation with the visible light of appropriate wave length thereby producing the oxidative product.

The invention is based on the charge-transfer photochemistry of hydrocarbon-oxygen collisional pairs which was discovered to occur in an appropriate but restricted environment. A solvent free cation exchanged alkali or alkaline-earth zeolite matrix is such an environment.

I. Zeolite Matrices

Zeolites are crystalline aluminosilicates forming a network of molecular-size channels or cages. These channels or cages form a zeolite matrix presenting diffusional constraints. These constraints prevent radical coupling reactions resulting in nonselectivity undesirable in oxidative processes. Poorly shielded extra-framework cations in the zeolite channels or nanocages create large electrostatic fields in their vicinity that were found to strongly stabilize the highly polar charge-transfer states of hydrocarbon-oxygen collisional pairs with their dipole aligned parallel to the field. Such stabilization of the radical cation-oxygen states render them accessible to visible light at low or room temperature and to thermal excitation in darkness at room or higher temperatures. Long-wavelength visible photons generate the primary photoproducts with the least amount of excess energy, and their use minimizes homolytic bond rupture and occurrence of random coupling reactions and prevent secondary photolysis leading to product decomposition and overoxidation.

A. Zeolite Materials

Zeolites are crystalline aluminosilicate minerals with the general formula

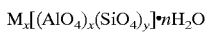

$$M_x[(AlO_4)_x(SiO_4)_y] \cdot nH_2O$$

which give rise to a structure based on a three dimensional network of $[AlO_4]^{5-}$ and $[SiO_4]^{4-}$ tetrahedra linked to each other via doubly bridging oxygen atoms. The network of alumina and silica tetrahedra gives rise to the porous cages-like nature of zeolite matrices, making zeolites widely used as sorbents, ion exchange media, catalysts and catalyst supports. Cations denominator represented by the M in the foregoing generalized equation are present in order to compensate for the otherwise excess negative charges in zeolites.

The cations are mobile and occupy various exchange sites depending upon their radius, charge, and degree of hydration. They are conveniently exchanged with other cations. Cations are selected from the group comprising alkali metals such as hydrogen, lithium, sodium, potassium, cesium and rubidium, alkaline earth elements, such as magnesium, calcium, barium and strontium and transition elements such as lanthanum. However, if suitable, any cation may be used. While zeolites are preferred, any porous solid material with molecular size cages featuring strong electrostatic fields may be used.

Preferably, cation M is selected from the group consisting of sodium, calcium, barium, potassium, lithium, lanthanum, or their combination.

Denominator n in the above equation varies from about 0 (in the anhydrous form) to about 10 in anhydrous zeolite and to about 250 for hydrated zeolite. Denominators x and y vary depending upon the zeolite or other solid support used. For instance, in the case of zeolite Y, x typically has a value of 56 and y typically has a value of 136.

The zeolites used in accordance with the present invention are obtained from either natural or synthetic sources, and may contain different aluminium to silicon ratios. Various ion exchanged forms may also be used, as well as different configurations of zeolites such as zeolite Y, L, and the more common pentasils such as pentasils ZSM-5, ZSM-11 and ZK-4 which are commercially available for example from Aldrich, Madison, Wis. Other types of molecular sieves such as aluminum phosphates, silica-aluminum phosphates, or molecular sieves obtained from Mobil Corporation, Cleveland, OH., may also be used. The zeolite of type Y or L are preferred for the instant invention.

Zeolite have cavities consisting of a three-dimensional network of molecular cages having a diameter of approximately 13 angstroms (Å), interconnected by window openings having a diameter of approximately 8 angstroms (Å), have a variable ratio of silicon to aluminum (Si/Al) and univalent cations present in the nanocages.

Y-type zeolites, also called Y-type faujasites, by contrast, generally compensate the negative charge introduced by the aluminum atoms of the zeolite cage walls with cations other than Si or Al. In faujasite NaY, for example, the Si/Al ratio is approximately 2.5, and there are seven $Na^+$ per nanocage (as many as 56 Na ions per unit cell). Electrostatic charges for NaY and other substituted zeolites are therefore much higher. The electrostatic field strengths for CaY, BaY and NaY zeolites have been determined to be 1.0 V/Å, 0.9 v/Å and 0.3 V/Å, respectively. The Y or L type zeolites are useful for the thermal or photooxidation processes of the current invention and are preferred because of the high electrostatic fields present inside the nanocages. Other zeolites or solid supports that have internal electrostatic fields of similar strengths to the faujasite zeolites used in the present work may also be used in accordance with the present invention.

Electrostatic fields of strengths of from at least 0.15 V/Å to about 2.0 V/Å, as determined by induced infrared absorption of nitrogen for measurements of electrostatic fields within the nanocages, are needed. Values above about 0.5 to about 1.0 V/Å for electrostatic field potentials are preferred.

The electrostatic fields present in the zeolites are fine-tuned for thermal oxidation or photooxidation, as needed, by the choice of the alkali, alkaline earth or transition element ions selected for incorporation into the nanocages. Enhancement of the electrostatic field within the zeolite nanocages is advantageously achieved, for example, by substitution of $Na^+$ by a smaller cation such as $Li^+$, or by a bivalent cation such as $Mg^{2+}$ in place of $Ba^{2+}$, (for example, changes properties of zeolites and permits access to thermally or visible light-induced oxygenation reactions of small hydrocarbons). The electrostatic charges that are subsequently generated within the zeolite nanocages thus cover a wide range, and are therefore used to stabilize species towards oxidation reactions over a wide range of ionization potentials.

Selection of appropriate zeolite for the most optimal oxidation of individual hydrocarbon is, within the frame of this invention, within the skills of the artisan.

It has now been found that a solvent-free cation-exchanged zeolite is an environment conducive for hydrocarbon-oxygen gas phase thermal or photochemistry.

Zeolite network of molecular-size channels or cages presents diffusional constraints that prevent undesired radical coupling reactions that dominate the chemistry in conventional fluid media. The poorly shielded extra-framework cations of alkali or alkaline-earth zeolites create large electrostatic fields in their vicinity that stabilize the highly polar charge-transfer of hydrocarbon•$O_2$ collisional pairs with their dipole aligned parallel to the field. Such stabilization of the radical cation•$O_2$— states renders them accessible to visible light at room temperature, or to thermal excitation at modestly elevated temperatures. Use of long-wavelength visible instead of UV photons guarantees generation of the primary photoproducts with the least amount of excess energy, thus minimizing homolytic bond rupture and random coupling reactions resulting in byproduct formation. Secondary photolysis leading to product decomposition and overoxidation is prevented.

Zeolite Y has a three-dimensional network of 13 Å-diameter cages which are connected by 8 Å windows. The wall of each cage carries a formal negative charge of 7, which is counterbalanced by 3–4 $Ba^{+2}$ ions located inside the cage. These cations are poorly shielded and hence give rise to very high fields inside the cage. The electrostatic field in BaY was determined experimentally by measuring the induced infrared fundamental absorption of $N_2$ and $O_2$ gas loaded into the zeolite. These infrared forbidden modes become active in the presence of the cage electrostatic field, and the magnitude of the field is determined from the band intensity. The average field experience by these molecules inside the cages of BaY is 0.8 V $AÅ^{-1}$.

The discovery of zeolite structures providing inducible conditions for thermal and photooxidation of hydrocarbons leads to selective oxidation of unsubstituted or substituted linear or branched alkenes, alkanes, or alkyl substituted cycloalkyls or aromatic hydrocarbons.

Any and all combinations of all types of zeolites, with cations or combinations thereof, are intended to be within the scope of the invention as long as the zeolite has a nanocage structure and electrostatic field of at least 0.15 V/Å.

B. Preparation of Zeolites

Preparation of the zeolites which are used as supports in the thermal or photooxidation reactions according to the invention is straightforward. The zeolites are dehydrated with mild heat treatment under vacuum to drive off absorbed water and are prepared generally as described in Examples 1 and 2.

Typically, temperatures of 100° C. to 500° C. are used. More preferably, used temperatures are mild of between about 150° C. to 250° C. Most preferably, zeolites are heated under vacuum at about 200° C. The zeolites are heated for approximately 12 to 16 hours under vacuum. Heat treating the zeolites below 25° C. under vacuum prevents the generation or activation of acidic sites within the zeolites. After heat treatment, approximately 99% of the absorbed water has been removed.

The above-described mild heat pretreatment of zeolites is contrary to conventional methods for the preparation of zeolites which involve heat treatment for prolonged periods of time of several days, usually at higher temperatures, in the presence of oxygen, or under other conditions conducive to the generation of Lewis acidic sites in the matrices. The absence of Lewis acid sites achieved by the above pretreatment, due to the mild treatment of the zeolites, is crucial to the high selectivites found in the processes of the present invention.

The selectivity of photochemical or thermal reactivity of alkanes in alkaline-earth zeolites to the concentration of residual water is shown in FIG. 1. FIG. 1 is a graph showing FT-infrared spectra of NaY, BaY, and CaY pellets in the $H_2O$ bending region upon loading of water from the gas phase.

A series of experiments was conducted to determine the concentration of remaining $H_2O$ in BaY and CaY pellets after a typical dehydration procedure. The exact procedure for dehydration is described in Example 2. An ideal infrared absorption of water for these measurements is the relatively narrow and moderately intense bending mode at 1640 $cm^{-1}$. In order to determine the extinction coefficient of this band, small, known amounts of water vapor, measured by manometric techniques, were absorbed into the dehydrated zeolite and infrared spectra recorded. The weight of the pellet was obtained by transferring it after the infrared measurement into a closed glass container of 100% humidity. The pellet was left for several days in this environment to assure complete hydration. The weight of the dry pellet was calculated from that of the hydrated zeolite by assuming 26% water content (by weight). From these data and the known density of supercages in zeolite Y ($3.8 \times 10^{20} g^{-1}$), the number of $H_2O$ molecules per supercage was calculated.

Results are close to those reported for the extinction coefficient of the $H_2O$ infrared bending mode in zeolite NaY reported in *J. Phys. Chem.*, 67:1621 (1963). A loading level of 0.3 $H_2O$ molecules per supercage of BaY or CaY was found following standard treatment of 10 hours dehydration at 200° C. under high vacuum. FIG. 1 shows the $H_2O$ bending absorption at 1640 $cm^{-1}$ with the intensity of each spectrum normalized to one $H_2O$ molecule per supercage. The integrated intensities are about the same in all three zeolites, although the band is appreciably broader in CaY than in BaY or NaY.

Using the above-described infrared method, water levels are easily and accurately varied to fit the most optimal conditions for hydrocarbon oxidation. Since the electrostatic field inside of the zeolites is important for successful photo or thermal oxidation, the infrared method for estimating electrostatic field strengths in the zeolites used for hydrocarbon oxidations was employed. Infrared absorption of $N_2$ induced by the electrostatic field in the vicinity of cations in zeolite type Y or L are shown in FIG. 2.

FIG. 2 shows the infrared absorption of the fundamental vibration of $N_2$ gas occluded in zeolite NaY, BaY, KL, and BaL. FIG. 2A shows zeolite BaY (I) and NaY (II). The spectra were recorded at 195 (potassium) (K), and the loading level corresponds to 1.3 $N_2$ molecules per supercage. FIG. 2B shows zeolite BaL (III) and KL (IV). Large signal is BaL (80% of $K^+$ exchanged by $Ba^{2+}$); small signal is KL. The spectra were recorded at 123 K, and the $N_2$ concentration was the same in two zeolites. FIGS. 2C and 2D shows structures of zeolite Y and L. The transition seen in FIG. 2 is infrared inactive for the free gas, but gains intensity in the vicinity of a poorly shielded cation because of the dipole induced by the electrostatic field. Intensities are proportional to the square of the field strength experienced by the molecule, and values of 0.3 V $Å^{-1}$ and 0.9 V $Å^{-1}$ were derived from such measurements for NaY and BaY. The interaction of the high electrostatic field with the large dipole generated upon excitation of the olefin•$O_2$ pair to the charge-transfer state results in a stabilization of the excited state by 1.5 eV for orientation parallel to the field and are generally between 1 and 3 eV depending on hydrocarbon and exchanged cation. The result is a very large red shift of the absorption from the UV into the visible region. This electrostatic field effect of the zeolite cage on the charge-transfer absorption that allows access hydrocarbon oxidation by visible light or by a temperature increase.

C. Loading and Function of Zeolites

The hydrocarbon starting materials used in the thermal or photooxidation processes of the present invention are generally loaded onto zeolites by introducing approximately 5–20, preferably 10 micro mols ($\mu$mol) of the material onto about a 10 mg structure of the zeolite. Given the internal zeolite parameters and the weight of the pellet used, this corresponds to a hydrocarbon concentration of approximately 1.5 molecules per nanocage. Loading of hydrocarbon materials onto support matrices is generally kept between 0.5 and 5.0 molecules per nanocage, and more preferably, between about 1.0 and 3.0 molecules per nanocage. Temperatures during the loading process are generally kept at room temperatures, but thermal oxidation or photooxidations were also successful following loading temperatures as low as −50° C. or +50° C.

For testing, the small pellet size was chosen as a matter of convenience, as the pellet could subsequently be mounted in a sample cavity of a Fourier-transform infrared (FT IR) instrument to facilitate monitoring of the reactions. For large scale thermal or photooxidation conversion, the zeolite matrix is suitably large and of shape to achieve the highest rate of hydrocarbon conversion.

Other amounts of hydrocarbon starting materials, zeolite matrix sizes and different zeolite configurations are also conveniently used and are intended to be within the scope of the invention.

II. Hydrocarbons Materials

The thermal oxidation in darkness or light-induced photooxidation reactions described herein are suitable for the oxidation of the majority of small hydrocarbon starting materials as long as they meet certain criteria.

One criterium for the success of the current invention is the ionization potential of the hydrocarbon used. A wide variety of hydrocarbon molecules may be successfully oxidized via thermal or visible light-induced photooxidation, provided that the zeolite is capable of stabilizing the hydrocarbon•$O_2$ contact pair which is formed with the zeolite. In case of photooxidation it is essential that ionization potential of the hydrocarbon give rise to a charge-transfer state for the absorbed hydrocarbon•$O_2$ moiety which lies within the visible range, by virtue of the stabilization of the electrostatic charges associated with the zeolite nanocage. If the ionization potential of the starting material is too high, such that the charge-transfer of the $O_2$_bound contact pair lies outside the range of the visible spectrum, photooxidation according the process of the present invention will not occur.

In case of thermal oxidation, the charge-transfer mechanism is induced in the dark if electrostatic fields of the zeolite and thermal energies are sufficiently high to render hydrocarbon radical cation-oxygen state accessible in the absence of light. Temperatures of thermal oxidation are between about 20° C. and between about 150° C., preferably about 80° C.

According to the present invention, any small hydrocarbon molecule that can be absorbed into the nanocages of a support matrix can be used to initiate the thermal or photooxidation reactions described herein. In general, any hydrocarbon able to diffuse through the nanocage openings of the support matrix, regardless of number of atoms, is suitable to be used. In general, hydrocarbons having as many as 100 atoms, preferably those having under 50 atoms, and most preferably those having less than approximately 30 atoms are suitable for thermal or photooxidation conversion according to the invention.

According to the present invention, the hydrocarbons suitable for conversion according to the invention are hydrocarbons having from 1 to 20, preferably 1 to 10 carbon atoms for alkanes, and from 1 to 10, preferably 1–8 carbon atoms for alkenes, aromatics or cycloalkyls. The hydrocarbon may be aliphatic or branched and the invention comprises the process for oxidation conversion of all aliphatic or branched hydrocarbons derived from above described hydrocarbons. Exemplary of the alkanes are unsubstituted, alkyl substituted, aliphatic or branched alkanes such as methane, ethane, butane, propane, pentane, hexane, heptane, octane, nonane, decane and higher alkanes and their substituted or branched derivatives such as, for example, iso- or neo-derivatives isobutane, isopentane, neopentane, or alkyl substituted alkanes such as methylhexane, and such others. Exemplary of the alkenes are unsubstituted, substituted, aliphatic or branched alkenes such as alkyl substituted ethylenes such as 2-butenes or cis- or trans-tetramethylethylene (2,3-dimethyl-2-butene) and such others. Exemplary aromatics and cycloalkyls unsubstituted or alkyl substituted include cyclohexane, cycloheptane, cyclopropane, cyclopentene, cyclooctane and all alkyl cycloalkanes, or benzene, toluene, cumene, naphthalene, anthracene, ethylbenzene and such others. Either branched or linear forms of any of the foregoing hydrocarbons may be used.

Size constraints notwithstanding, there appear to be few restrictions regarding the nature of the starting material. Essentially, any hydrocarbon molecule or substituted hydrocarbon that meets the foregoing criteria of size, ionization potential and presence of alpha-hydrogen atoms for alkenes, may be used. Alkanes having from 3 to 10 carbon atoms are specially suitable for thermal oxidation or for thermal oxidation combined with photooxidation. Essentially all above described hydrocarbons are suitable for photooxidation according to the invention.

A strong stabilization of an alkene+•$O_2$- charge-transfer pair inside a zeolite cage arises from the interaction of its large dipole (about 15 Debye) with the high electrostatic field in the vicinity of alkali or alkaline-earth cations. In the case of NaY and BaY, there are 3–4 cations located in each supercage. The wall of the cage carries a formal negative charge of 7 which resides on the framework oxygens. The electric shielding of the cations in the supercage by the framework oxygen is poor, resulting in high electrostatic fields around the cations.

III. Process for Selective Oxidation of Hydrocarbons

The process for selective thermal or photooxidation of hydrocarbons comprises several steps:

1. The most suitable zeolite is selected either from type Y or L, specifically the NaY, BaY, CaY, KY or NaL, BaL, CaL or KL, depending on the required electrostatic fields. In this respect, the electrostatic field of Y type zeolite is NaY<BaY<CaY and NaL≈KL<BaL<CaL.

2. Zeolite is prepared for loading with hydrocarbons, by, for example, dehydrating the selected zeolite at mild conditions at a temperature of about 100–500° C., preferably about 200° C., for about 12 to about 16 hours under vacuum.

3. Hydrocarbon in its gas phase is loaded under pressure 1–500 Torr at about −50° C. to about +50° C., preferably at room temperature, in an amount of about 0.5–5, preferably 1.5 molecules of hydrocarbon per nanocage of the zeolite.

4. Oxygen is introduced under pressure for about 0.66 atm to about 4000 atm. The higher the pressure, the higher the reaction rate.

5. Oxidation of the hydrocarbon is induced either by submitting the loaded zeolite matrix to a light, such as visible light or broad band sources within the same wavelength region, that is blue or red light at about −100 to about 80° C., preferably at room temperature, or submitting the loaded zeolite matrix to the thermal oxidation in darkness by letting the oxidation reaction proceed at room temperature of about 20° C. to about 150° C., preferably at about 80° C., for several minutes to several (up to 10) days, preferably about 3–5 hours.

IV. Process For Thermal Oxidation of Hydrocarbons

The process for thermal oxidation involves providing conditions conducive to oxidation of hydrocarbons loaded into zeolite matrix and submitted to temperature suitable for thermal conversion of hydrocarbon to its oxygenated derivative.

The charge-transfer mechanism of the visible light-induced photooxidations in zeolites is induced in the dark when electrostatic fields are sufficiently high to make spontaneous formation of radical cations and $O_2^-$ accessible. Such dark thermal oxidation has been found in low alkanes, such as cyclohexane in NaY at temperatures higher than 50° C., and isobutane and propane in BaY at temperatures higher than 50° C. or CaY room temperature. Oxidation products in these instances were cyclohexanone, t-butylhydroperoxide and acetone, respectively. Selectivity in terms of these products was complete even at higher than 30% conversion of the alkane and a temperature as high as 150° C. (propane in BaY). These are the first selective thermal oxidations of small alkanes achieved by any method.

There are certain requirements which both the zeolites and hydrocarbons must meet for successful thermal oxidation.

Zeolite must have unshielded or poorly shielded cation sites with a strong electrostatic field of at least 1 V/Å. A charge-transfer mechanism of the thermal oxidation in darkness involves cation sites with especially strong electrostatic fields and poor shielding cation. The high mobility of alkane and oxygen molecules in the zeolite allows easy access to such sites. At these most poorly shielded cation sites, spontaneous charge-transfer results in alkane radical cation and $O_2^-$ formation. Hydrocarbon must have low ionization potential for thermal oxidation in zeolite NaY. The fact that this process occurs in zeolite NaY with cyclohexane but not with propane is consistent with the considerably lower ionization potential of cyclohexane (9.8 eV) compared to propane (11.1 eV). Moreover, the observation that propane reacts faster in CaY than in BaY, and not at all in NaY is consistent with the increasing fields in NaY<BaY<CaY. For example, when ionization potential of hydrocarbon is lower then 10 eV, then zeolite must have at least 1 V/Å. These and other variations of the process are intended to be within the scope of the invention.

Zeolites suitable for thermal oxidation should have none or very little residual water. Increased concentration of residual water in the zeolite gradually quenches the thermal reaction, which reflects the shielding of coulombic interactions by $H_2O$. All these findings support charge transfer from alkane to $O_2$ as the initial reaction step.

Thermal oxidation according to the current invention thus provides a highly selective process for conversion of hydrocarbons to their respective oxygenated derivatives. The thermal oxidation is highly selective as it results in only one majority (at least 95%) product without production of any byproducts, and without possibility of further conversion or degradation of the final product. Yields of the final product are much improved against prior methods.

V. Process for Photooxidation of Hydrocarbons

The process for photooxidation of hydrocarbons involves irradiation of the loaded zeolite matrix with visible or infrared light.

The absorption of hydrocarbons and molecular oxygen onto the zeolites results in a red shift of the absorption characteristic of hydrocarbon•$O_2$ charge-transfer moiety to the visible region. As a result, any source which provides light within the visible spectrum is suitable to be used to initiate photooxidation, including light having wavelengths of about 400 nm to about 700 nm (4000–7000 Å), and particularly light having wavelengths between about 425 and about 675 nm.

Tunable continuous wave (CW) lasers are typically used to initiate the photooxidation reactions of the present invention, as well as other broad band, conventional visible light sources, filtered or non-filtered. For example, the blue-light irradiation of toluene•$O_2$ absorbed onto zeolite BaY results in the formation of benzaldehyde as the sole reaction product; trans-2-butene•$O_2$ absorbed onto NaY and irradiated with green light gives exclusively 3-hydroperoxy-1-butene; pure hydroperoxides are obtained at –50° C. via treatment with $O_2$ under unfiltered visible light, without the need for additional catalysts. Photooxidation reactions with blue light were also observed for other hydrocarbons, such as propylene, isobutane, and cyclohexane on a variety of supports. The products obtained were allyl hydroperoxide (AHP), tert-butyl hydroperoxide and cyclohexyl hydroperoxide, respectively. Other hydrocarbons which were also successfully photooxidized upon irradiation with blue-green light include ethyl benzene, cumene, toluene, propane, ethane and methane, etc.

Generally, photooxidation reaction rate at a constant wavelength decreases with increasing ionization potential of the hydrocarbon starting material. However, a determining factor as to whether reaction takes place at a reasonable rate is dependent upon the mechanism of the reaction. The key step is the proton transfer from the hydrocarbon radical cation to the $O_2$.

The temperatures at which the light-induced photooxidations of the present invention is carried out can vary over a wide range. Typically, temperatures may conveniently be varied from a low temperature of about –100° C. to about 80° C., preferably about –50° C. to a high of about +30° C. Reactions have been conducted at temperatures as low as –100° C. for propylene and as high as 80° C. for toluene loaded into BaY.

Time at which the hydrocarbon is submitted to the visible light varies from several minutes to several days, however, the shorter time period is preferred for practical purposes. The typical and preferred time period is from several minutes to about 10 hours. The length of time is conveniently shortened by increasing the intensity of the light.

The visible light-induced photooxidation process of hydrocarbon•$O_2$ complexes adsorbed onto zeolites according to the present invention is efficient. For example, the quantum efficiency for the treatment of toluene•$O_2$ on CaY with blue light at 488 nm enabled estimation of the quantum efficiency of the reaction to be on the order of 10%. This is a high quantum yield for the conversion of toluene to benzaldehyde, and represents a distinct improvement over the current prior art processes. The currently available prior art processes provide selective conversion higher then 90% selectivity at about only 1% or less of conversion. The current process provides higher than 95% selectivity at conversion higher than 35%. The process of the invention thus has both higher selectivity and also substantially higher conversion.

Additionally, the process of the invention does not proceed beyond the desired oxidative product. Commercial processes often continue to convert the obtained product or utilize other pathways to oxidate the hydrocarbon. For example, commercially used process for the production of benzaldehyde in solution proceeds via a costly $Co^{3+}$-catalyzed route, and results in the continued oxidation conversion of the aldehyde product to benzoic acid rather than to desired benzaldehyde.

The quantum efficiency for the photooxidation of propylene in zeolite BaY at 488 nm to give exclusively allyl hydroperoxide (AHP) is even more efficient. In this instance, the quantum efficiency was estimated to be approximately 20%. These high quantum yields are crucial for the usefulness of the described photooxidation reactions of the present invention.

Photooxidation according to the current invention thus provides highly selective process for conversion of hydrocarbons to their respective oxygenated derivatives. The photooxidation is highly selective as it results in only one majority (at least 95%) product without production of any byproducts, and without possibility of further conversion or degradation of the final product. Selectivity and yields of the final desired product are much improved against prior methods.

VI. Combined Thermal and Photooxidation of Hydrocarbons

Both thermal oxidation and photooxidation methods are conveniently combined to achieve the highest rate of conversion of the hydrocarbon to its oxygenated derivative. Combination is performed in both modes, that is the loaded zeolite with hydrocarbon and oxygen may be first submitted to thermal reaction and then photooxidation or vice versa or both may be performed simultaneously.

VII. Thermal or Photooxidation of Specific Hydrocarbons

Thermal and photooxidation performed under various conditions was discovered to exist for hydrocarbons such as alkanes, alkenes and aromatic or cyclo alkanes.

A. Thermal Oxidation and Photooxidation of Alkanes

A proposed mechanism for alkane thermal oxidation and photooxidation is seen in Schemes 1 and 2.

Scheme 1 shows the mechanism for alkane photooxidation.

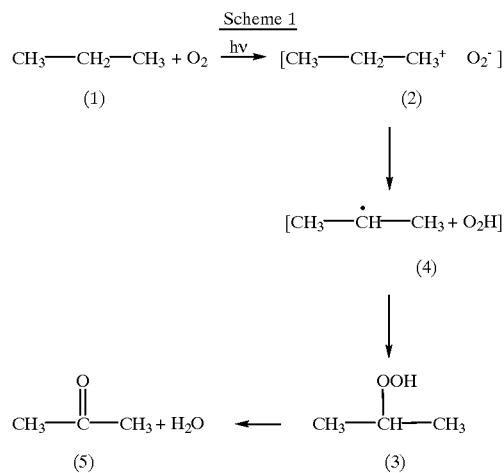

Scheme 1 shows a propane (1) photooxidation, where the initial step is proton transfer from the alkane radical cation to $O_2^-$ (2). The alkane cation radical is formed by photoexcitation. Alkane radical cations generated upon photoexcitation are spectroscopically observed species that have a very high propensity for deprotonation to form alkyl radicals. Proton transfer from the radical cation to $O_2^-$ is rapid because of the high acidity of the cations. The alkyl hydroperoxide (3) emerging from recombination of the alkyl and $H_2O$ radical (4) dehydrates spontaneously in the ionic zeolite. The $H_2O$ elimination results in ketone in Scheme 1 acetone (5) production.

Scheme 2 shows proposed mechanism for alkane thermal oxidation.

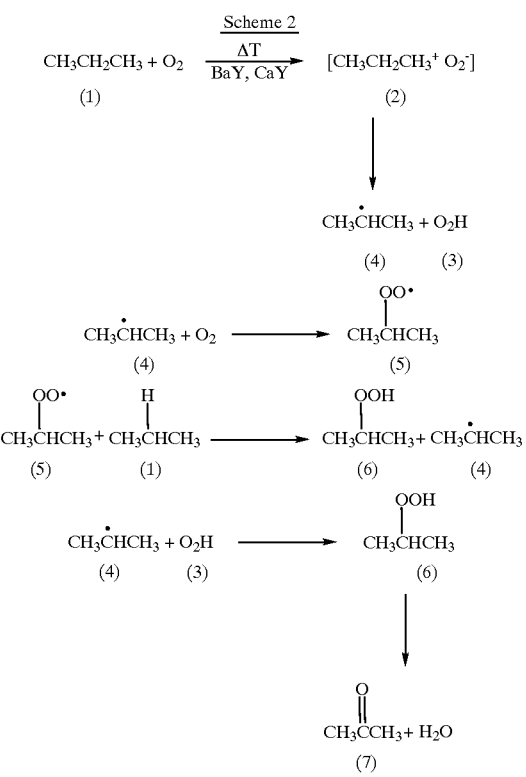

Scheme 2 illustrates thermal conversion of propane (1) to acetone (7). The initial step which accompanies excitation of the charge-transfer state is fast proton transfer from the propane (1) to alkane radical cation and $O_2^-$ (2) to yield an alkyl radical (4) and $HO_2$ radical (3), similarly to the photolysis process. Propane and ethane radical cations are spectroscopically established species. Alkane radical cations in general are known to be highly acidic and therefore have a very strong tendency for proton transfer to a base like $O_2^{31}$. Reaction of radical (4) so produced with $O_2$ yields alkyl peroxy radical (5), which in turn reacts in chain propagation with a new propane yielding isopropyl (ethyl) hydroperoxide (6) and another alkyl radical (4). Termination of the chain occurs by combination of radical (4) with radical (3) producing hydroperoxide (6). Heterolytic thermal rearrangement of the hydroperoxide (6) results in the production of the desired product acetone (7) and $H_2O$. The thermal conversion process in Scheme 2 is thus an on-going chain propagation which needs no catalysts or irradiation in order to proceed. As long as the temperature is kept the same, the thermal reaction proceeds. The reaction is terminated by decreasing the temperature.

At elevated temperatures, sufficient energy is available to overcome 18 kcal mol-1 activation energy for H abstraction from alkane via chain propagation reaction.

Figure 3:
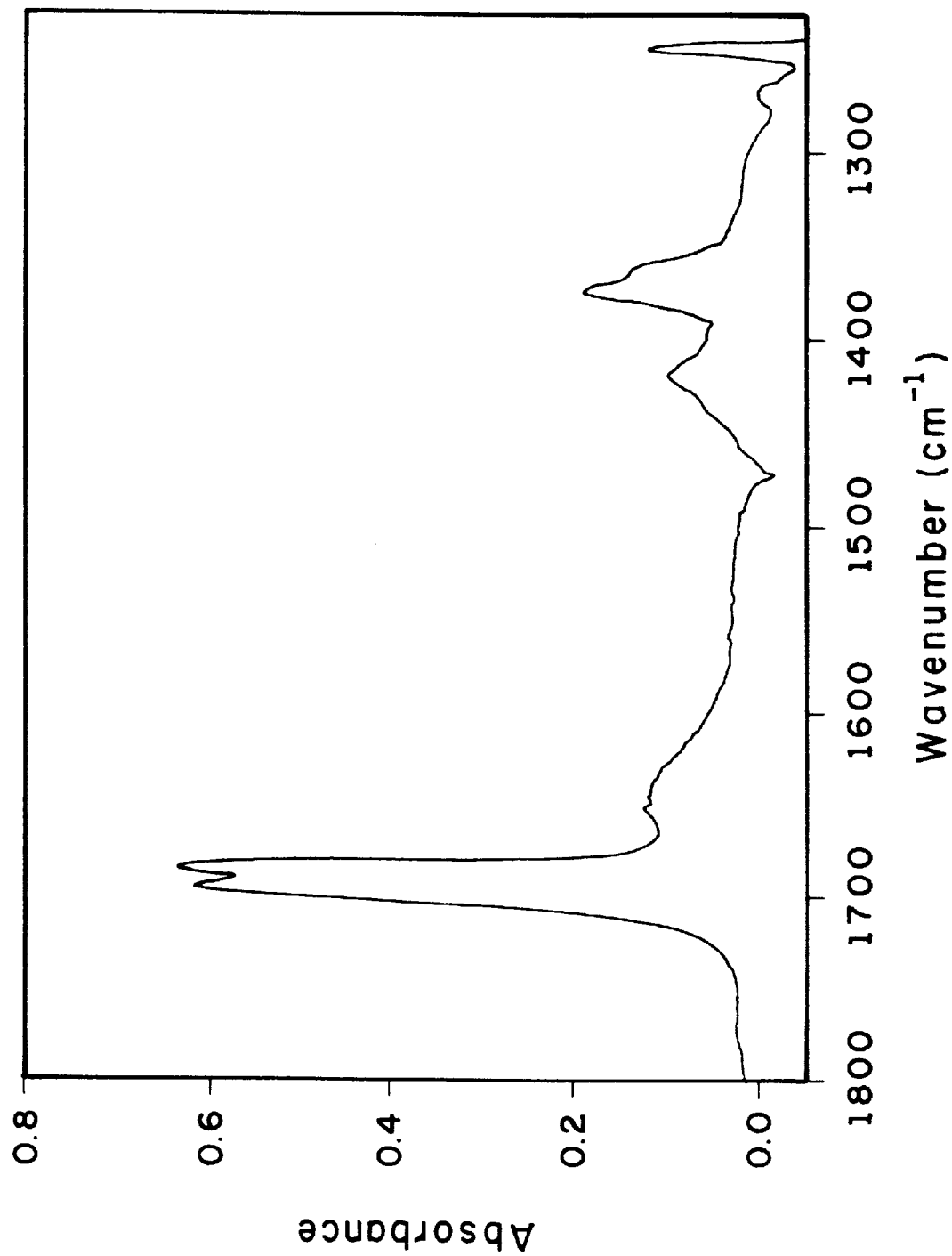
FIG. 3 illustrates thermal oxidation of propane. FT-infrared difference spectrum after 5 hours reaction at 21° C. in CaY pellet loaded with 150 Torr propane and 1 atm $O_2$.

Thermal oxidation of alkane, represented by propane, in CaY zeolite is shown in FIG. 3.

FIG. 3 represents FT-infrared difference spectrum after 5 hours reaction at 21° C. in a CaY pellet loaded with 150 Torr propane and with 1 atm $O_2$. Upon loading of propane and $O_2$ into zeolite CaY, thermal reaction was observed at room temperature just minutes after introducing the hydrocarbon and oxygen gases into the zeolite matrix. Product bands at 1700, 1689, 1420, 1375, 1365, and 1246 $cm^{-1}$ originated from acetone as confirmed by comparison with the infrared spectrum of an authentic sample of acetone in CaY. The band at 1640 cm$^{-1}$ and a very broad absorption centered around 3400 cm$^{-1}$ are due to $H_2O$ coproduct. No other products were observed. Propane thus was oxidized in the dark by $O_2$ to acetone with complete selectivity. Moreover, propane was completely inert in CaY as long as no $O_2$ was added to the zeolite.

The 1700/1689 cm$^{-1}$ doublet of the C=O stretching absorption of acetone is attributed to two different sites of the molecule in the zeolite cage. At the earliest stage of the reaction, only the 1689 cm$^{-1}$ band was observed. The 1700 cm$^{-1}$ peak appears upon continued accumulation of acetone. The same phenomenon was observed when loading an authentic sample of acetone from the gas phase, which confirms that the strong v(C=O) product absorption originates exclusively from acetone.

Figure 4:
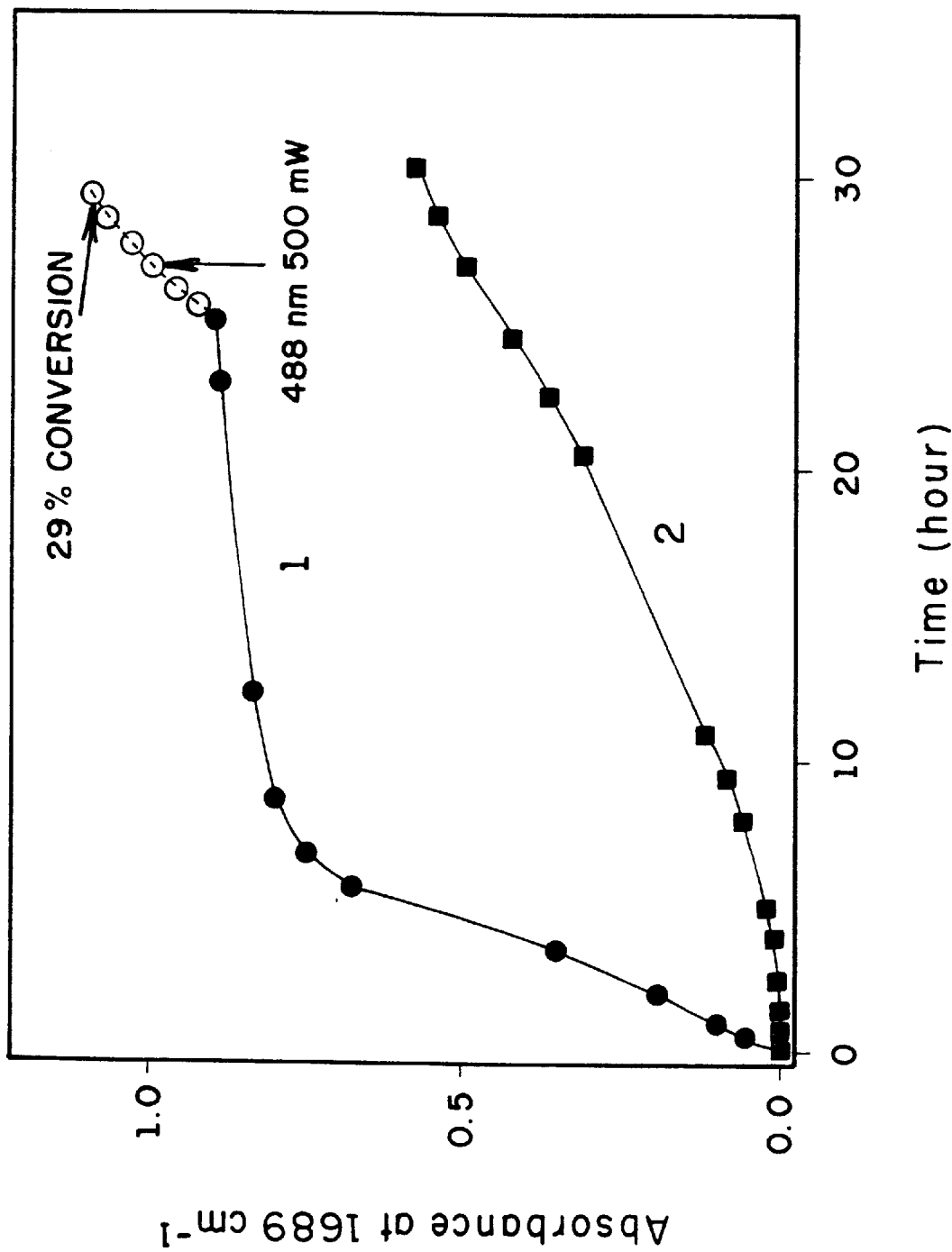
FIG. 4 shows kinetics of thermal propane oxidation in CaY at room temperature.

Kinetics of thermal propane oxidation in CaY at room temperature is shown in FIG. 4.

FIG. 4 shows kinetics of thermal propane oxidation in CaY at room temperature. Curve 1 shows acetone growth due to spontaneous oxidation in a pellet with 0.3 residual $H_2O$ molecules per supercage (filled circles), followed by blue light-induced growth (open circles). Curve 2 gives the thermal product growth in a CaY pellet containing 1.1 $H_2O$ molecule per supercage. Propane was loaded under 150 Torr pressure; oxygen was loaded under 750 Torr pressure.

As seen in FIG. 4, acetone absorbance growth at ambient temperature shows about 20% conversion of propane during the first 10 hours after loading of propane into the zeolite. This was achieved in a CaY pellet with 0.3 $H_2O$ molecules per supercage (curve 1). Thermal conversion levels off after that, but irradiation with blue light results in a new sharp increase of the yield (empty circles) also shown in FIG. 4. This shows that the combination of both methods is effective in increasing the yield of the final product.

The reaction up to 30% conversion of the alkane was monitored without noticing any degradation of the product selectivity. The residual water content strongly influences the thermal reaction as illustrated by curve 2 of FIG. 4. The curve 2 shows the acetone product growth in a CaY pellet with 1.1 $H_2O$ molecules per supercage under otherwise identical conditions as in trace 1.

Figure 5:
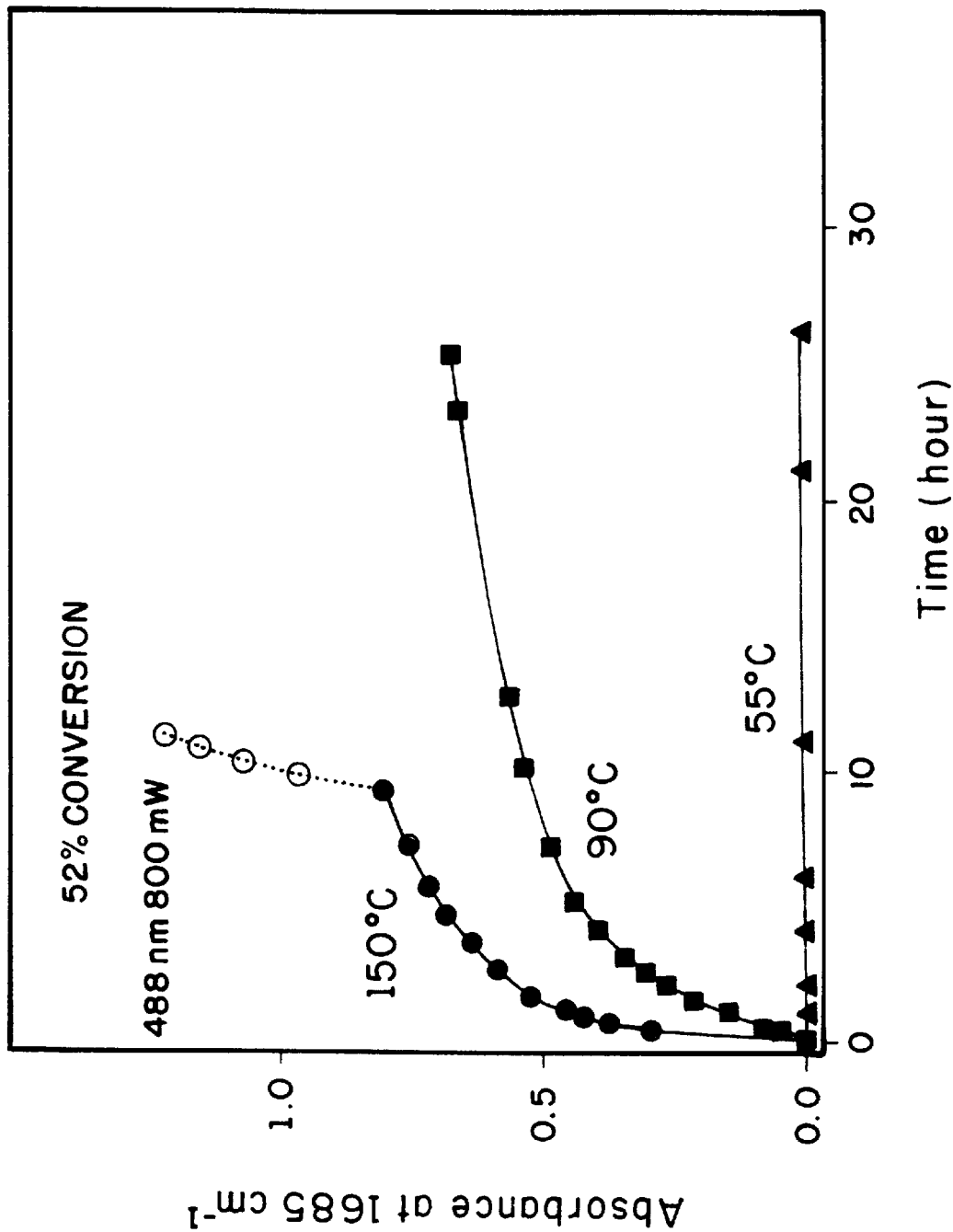
FIG. 5 is a graph of kinetics of thermal propane oxidation by $O_{2-}$ in BaY zeolite at elevated temperatures.

FIG. 5 is a graph showing kinetics of thermal propane oxidation in BaY at elevated temperatures. Curve 1 shows acetone growth at 55° C. in a pellet with one residual $H_2O$ molecule per supercage; curve 2 represents thermal growth, at 90° C.; curve 3 represents thermal growth at 150° C. (filled circles), followed by blue light-induced oxidation (open circles). Propane pressure was 150 Torr; oxygen pressure was 750 Torr.

No thermal oxidation of propane was observed in zeolite BaY at ambient temperature, even when exposing the pellet to 8 atm of $O_2$ for 10 hours. However, very slow thermal reaction was noticed at 55° C., and the rate increased sharply towards higher temperature. At 150° C., one third of the propane in the zeolite is converted in 9 hours, with acetone as the exclusive product. No loss of selectivity was observed upon subsequent irradiation with blue light for another 2 hours, reaching 52% conversion of the alkane. It is clear from the steep slope of the top growth curve in FIG. 5 that there is no sign of leveling off even at that point. In the case of zeolite NaY, no thermal autoxidation of propane was observed at temperatures as high as 150° C.

Thermal oxidation of alkanes proceeds in darkness and depends on the temperature, loading pressure of hydrocarbon and oxygen, and on the selection of the zeolite matrix as well as hydration of the zeolite matrix.

Photooxidation of alkanes proceeds at different conditions than that of thermal oxidation. This finding contributes to versatility of the invention. Conditions for oxidative conversion are thus amenable to manipulation dependent on properties of the hydrocarbon.

Figure 6:
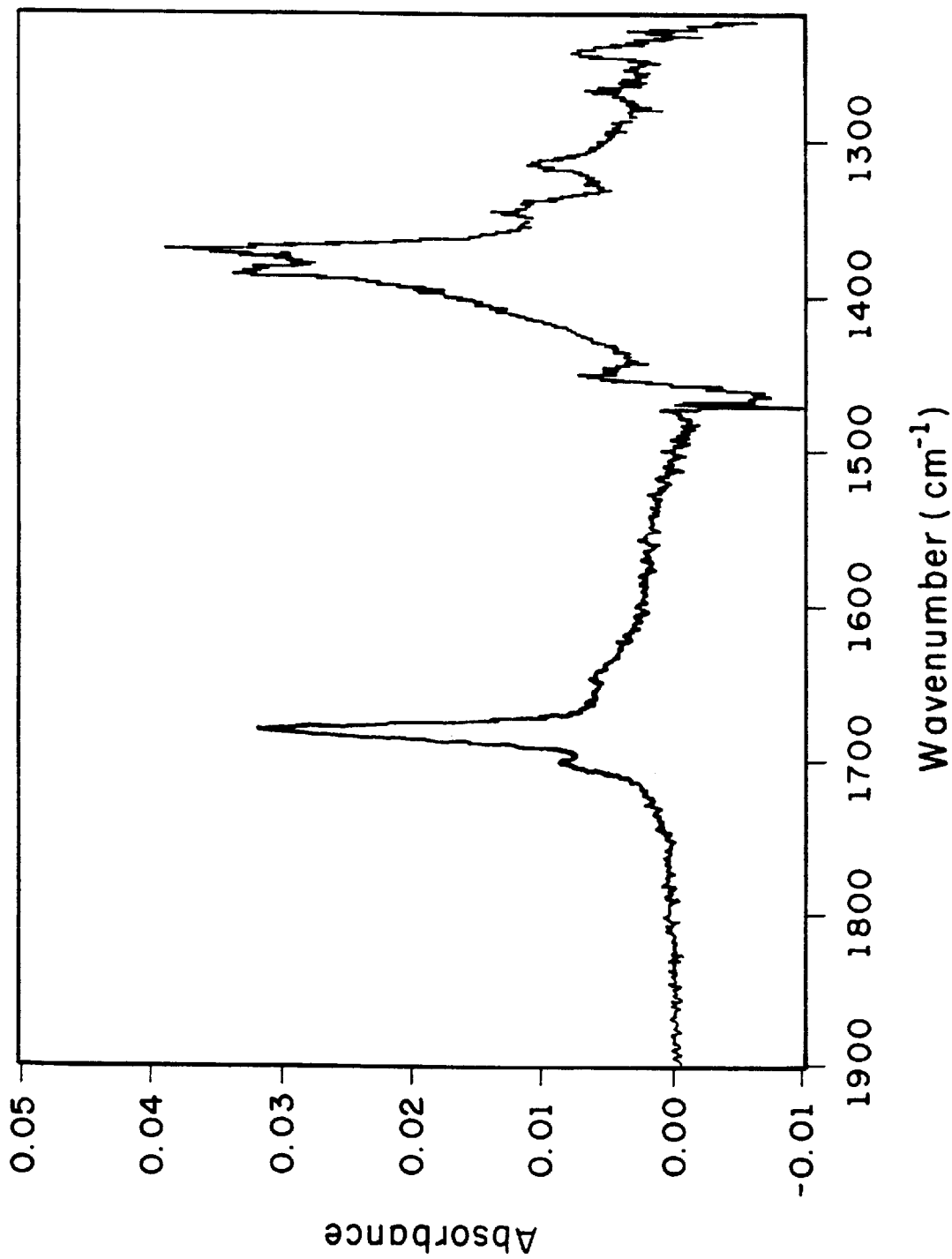
FIG. 6 is a graph showing photooxidation of propane.

An infrared difference spectrum showing reactant propane depletion and product acetone growth following 150 min photolysis at 488 nm (500 mW cm$^{-2}$) is depicted in FIG. 6.

FIG. 6 is a graph showing photooxidation of propane. Specifically, FIG. 6 is FT-infrared difference spectrum measured before and after irradiation at 488 nm (500 mW cm$^{-2}$) for 150 minutes at room temperature of a zeolite BaY pellet loaded with 300 Torr of propane and 650 Torr of $O_2$ gas.

All product absorptions (positive bands) are attributed to either acetone, water, or propyl hydroperoxide. Identification of acetone (1247, 1365 (shoulder), 1374, 1418, 1684, 1707 cm$^{-1}$ (shoulder)) and $H_2O$ (1650, 3470 cm$^{-1}$ (broad)) is based on comparison with infrared spectra of authentic samples loaded into BaY. All other product bands (1270, 1318, 1348, 1374, 1391, 1456, 1472, 3170 cm$^{-1}$ (broad)) decrease at ambient temperature in the dark under concurrent growth of compound having a composition $(CH_3)_2C=O$ and $H_2O$. Therefore, this thermally unstable intermediate has the composition $C_3H_8O_2$. The broad absorption at 3170 cm$^{-1}$ is characteristic for alkyl hydroperoxides in zeolite BaY and the bands in the fingerprint region agree well with alkyl hydroperoxide IR spectra previously reported.

Hydroperoxides with a H in $\alpha$ position have been shown to rearrange thermally to carbonyl compound and $H_2O$ at ambient temperature. The thermally labile product was propyl hydroperoxide. While distinction between primary and secondary propyl hydroperoxide cannot be made on the basis of the infrared data alone, the observed elimination of $H_2O$ to yield acetone allowed unambiguous identification of the intermediate as isopropyl hydroperoxide. No other product was observed even when monitoring the photochemistry up to 22% conversion of the propane and following the subsequent rearrangement of the isopropyl hydroperoxide intermediate to acetone. The conversion was calculated as the ratio of total product growth to amount of propane loaded into the zeolite matrix. Analogous experiments with propane-d8 confirmed acetone and water as the only final photolysis products.

Oxidation of another alkane, ethane, by $O_2$ was observed in $Ba^{+2}$ and $Ca^{+2}$-exchanged zeolites BaY or CaY. No thermal reaction occurred when ethane 250-500 Torr and 1 atm of $O_2$ was loaded into the dehydrated zeolite pellet. Compared to propane oxidation, photochemical reaction of ethane under visible light from a tungsten lamp or blue light from an Ar ion laser (488 nm) was slow in BaY. The product yield increased four-fold when conducting the reaction in zeolite CaY instead. An infrared difference spectrum of blue light driven ethane oxidation in CaY is shown in FIG. 7.

Figure 7:
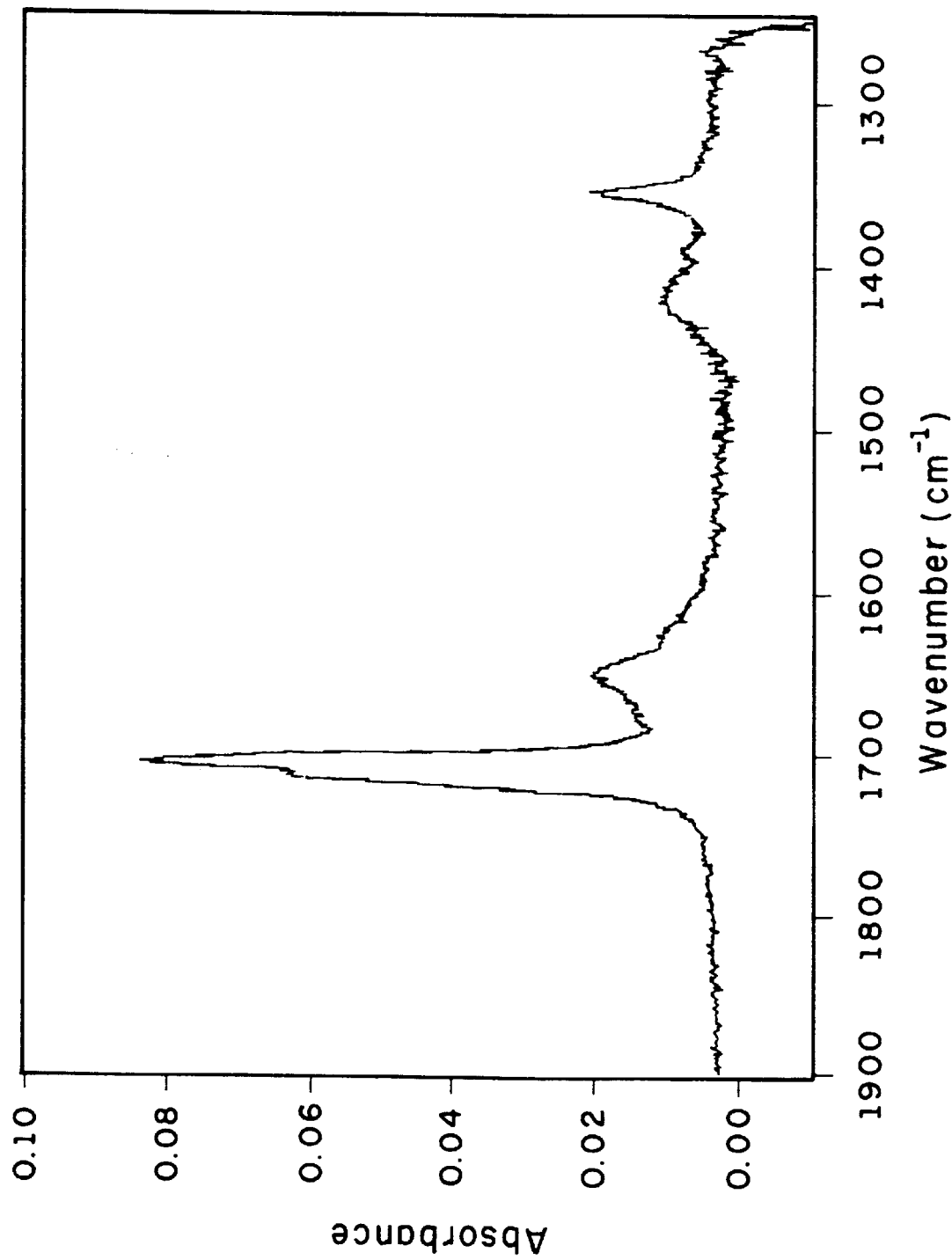
FIG. 7 is a graph showing photooxidation of ethane.

FIG. 7 is a graph showing photooxidation of ethane. Specifically, it shows FT-infrared difference spectrum before and after irradiation at room temperature of a zeolite CaY pellet loaded with 500 Torr ethane and 750 Torr $O_2$ gas at 488 nm (500 mW cm$^{-2}$) for 180 minutes.

As seen in FIG. 7, readily observed product bands at 1357, 1419, 1707, and 1716 cm$^{-1}$ (shoulder) originate from acetaldehyde, while the absorption at 1654 and 3400 cm$^{-1}$ is due to $H_2O$. These assignments were confirmed by recording of ethane-$d_6$ photooxidation in CaY. Identification of acetaldehyde was based on comparison with infrared spectra of authentic $CH_3CH=O$ and $CD_3CD=O$ samples in CaY. No final product aside from acetaldehyde and $H_2O$ was observed even at the highest recorded conversion of about 20%. Specifically, no $CO_2$ was produced. $CO_2$ is a major byproduct of any other method for ethane oxidation by $O_2$. This finding was confirmed by experiments using $^{13}C_2H_6$. $^{13}CO_2$ has an asymmetric strength absorption that is removed by a red shift of 65 cm$^{-1}$ from the absorption of atmospheric carbon dioxide traces in the spectrometer optical path.

Figure 8:
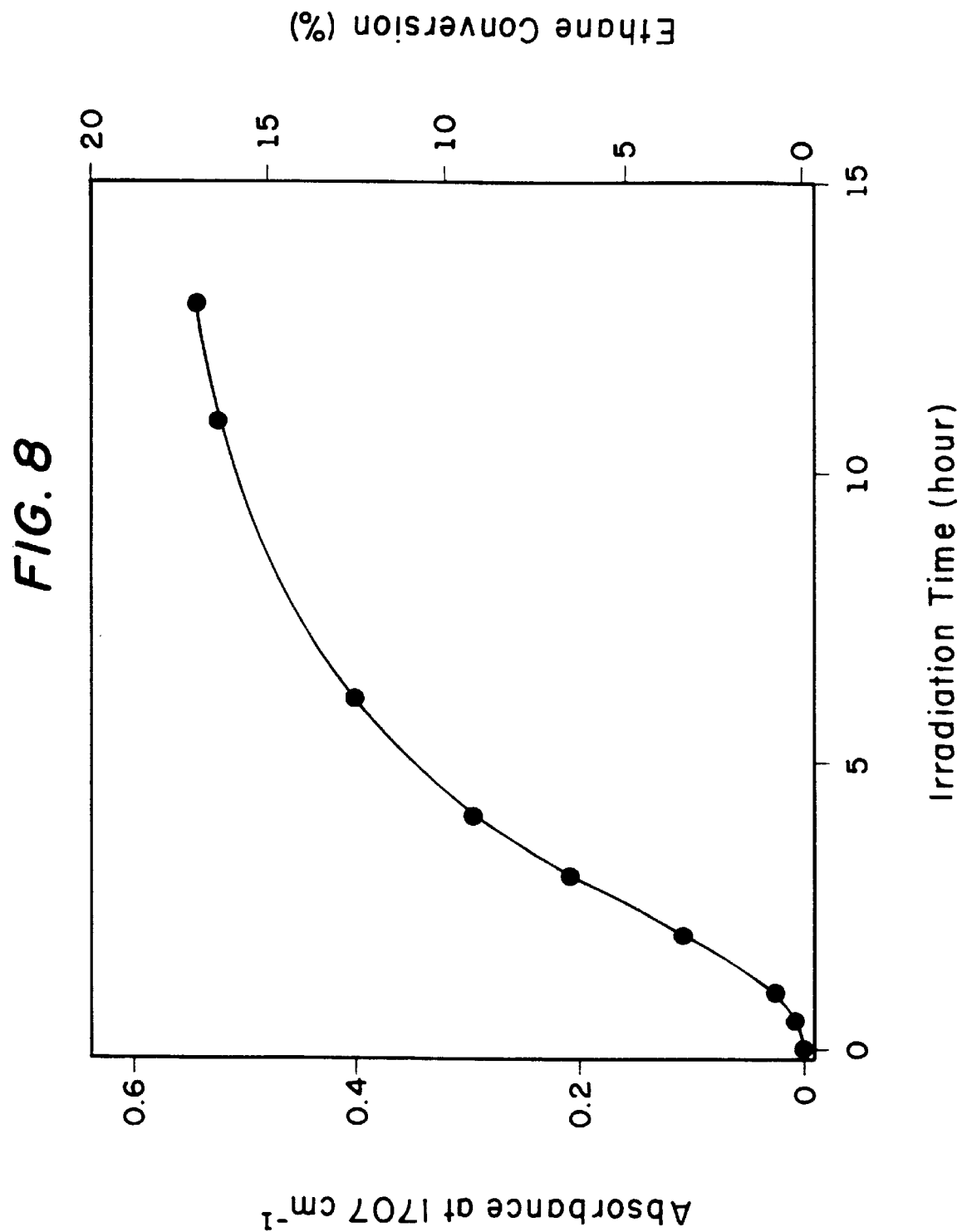
FIG. 8 illustrates acetaldehyde growth kinetics at 1707 $cm^{-1}$ upon irradiation at 488 nm of CaY loaded with ethane and $O_2$.

Acetaldehyde growth during photolysis exhibits an induction period as shown in FIG. 8. FIG. 8 illustrates acetaldehyde growth kinetics at 1707 cm$^{-1}$ (C=O stretch) upon irradiation at 488 nm (800 mW cm$^{-2}$) of CaY pellet loaded with 250 Torr of ethane and 750 Torr of $O_2$.

Results seen in FIG. 8 show that the aldehyde is formed via an intermediate. Indeed, when removing excess ethane and $O_2$ from the zeolite after photolysis and monitoring the matrix for several hours in the dark at room temperature, a slow growth of acetaldehyde and $H_2O$ was observed under concurrent decrease of very small bands at 1282, 1391, 1488, and 3200 cm$^{-1}$ (shoulder). The final products acetaldehyde and $H_2O$ show that the observed intermediate is ethyl hydroperoxide, and the infrared spectrum is consistent with this finding. Ethyl hydroperoxide is the primary photoproduct of blue light induced ethane oxidation by $O_2$ in CaY which thermally eliminates $H_2O$ to yield acetaldehyde as the sole final oxidation product.

The origin of the visible light-induced reaction of propane and ethane with oxygen is excitation of the alkane•$O_2$ charge-transfer state. When loading higher alkanes such as cyclohexane or isobutane together with $O_2$ gas into zeolite BaY or NaY, reflectance measurements give an optical absorption tail extending into the green spectral range (500 nm). This tail is due to the hydrocarbon•$O_2$ contact charge-transfer transition. The onset of the corresponding absorption in high pressure $O_2$ gas phase or $O_2$ saturated liquid alkane lies in the UV region below 300 nm. This implies a 2–3 eV red shift of the absorption onset in the zeolite. The large shift is caused by a strong stabilization of the polar charge-transfer state (alkane radical cation-$O_2^-$ pair, dipole approx. 15 Debye) by the high electrostatic field inside the zeolite cage.

The increase of the photochemical yield of ethane oxidation upon substitution of BaY by CaY is consistent with the higher electrostatic fields in the CaY cage as this results in a stronger stabilization of the ethane•$O_2$ charge-transfer state. However, while zeolite BaY can be prepared free of acid sites, this is not possible for CaY; the latter inevitably contains Brönsted acid sites. The product selectivity in the case of the ethane oxidation is not affected by these acid sites in any way.

The dark or thermal reaction of isobutane adsorbed onto BaY proceeded at a reasonable rate, with overnight conversion of approximately 5%. By contrast, the light-induced reaction of isobutane (10 Torr, 0.013 atm) and oxygen (760 Torr, 1 atm) adsorbed onto zeolite BaY at temperatures as high as 0° C. to room temperature gave tert-butyl hydroperoxide as the exclusive oxidation product with selectivities for the hydroperoxide greater than 99% at room temperature. If left within the BaY zeolite matrix, the tert-butyl hydroperoxide decomposed slowly, generating acetone and methanol.

Irradiation of the thermal reaction with blue laser light, or with a tungsten lamp at 200 mW, enhanced the rate of the initial reaction to form the hydroperoxide product by approximately a factor of 10 with no concomitant loss of selectivity. Light, therefore, can be used in tandem with the thermal reaction to enhance reaction rates.

Propane at 150 Torr (0.20 atm) was loaded onto a variety of dehydrated zeolite samples, after which 760 Torr (1 atm) of oxygen was subsequently added. After loading, the reactant system was left in the dark at room temperature for approximately 3 to 5 hours. While no dark reaction took place in BaY, some acetone formation was observed in CaY. The dark reaction reached an endpoint after approximately 24 hours. The conversion for the thermal reaction of propane in CaY was 30%. Acetone and water were the exclusive final products of the thermal reaction, as determined by in situ Fourier-transform infrared (FT-IR) spectroscopic analysis. These are decomposition products of the propane hydroperoxide which is initially formed, but has a very short half-life.

Upon irradiation at 488 nm or 514 nm (500 mW/cm$^2$) in CaY, the reaction rate of propane increased by a factor of approximately 5 compared to the dark reaction. Propane and oxygen loaded into zeolite BaY exhibit no reaction in the dark. However, when irradiated with a laser at 488 nm or 514 nm (500 mW power), the formation of acetone and water was observed. Longer visible light wavelengths may also be used. Again, these two species are the decomposition products of the initially formed propyl hydroperoxide. No other products could be detected by in situ FT-IR spectroscopy. The conversion was followed up to approximately 20%.

In other zeolites or under different reaction conditions, i.e., higher oxygen pressure (10 atm) higher conversions are reached.

Ethane was photooxidized or thermally oxidized as follows. A CaY zeolite sample was filled with 300 Torr (0.39 atm) partial pressure of ethane, after which 760-1320 Torr (1–2 atm) oxygen was added. Irradiation of the zeolite pellet with laser light at 458 nm resulted in the formation of acetaldehyde and water, exclusively. Longer wavelengths may also be used. Both acetaldehyde and water are decomposition products of the initially formed ethyl hydroperoxide. No other reaction products were found. The conversion was followed up to about 20%. No intrazeolite acetaldehyde polymerization was observed within the time scale of the reactions, which were generally conducted within 24–48 hours. One possible explanation for the absence of any polymerization product may be that the acetaldehyde concentration is not more than one molecule per nanocage (i.e. one mole/liter). Higher conversions and faster reaction rates may be obtained with other zeolites under different reaction conditions.

Reaction under conditions similar to those used for ethane was used for methane as the starting hydrocarbon. Such reaction resulted in the formation of formaldehyde and water. Prolonged photolysis led to the formation of formic acid. The process of the invention is, therefore, also suitable for production of forming acid from methane.

B. Thermal and Photooxidation of Alkenes

Selective thermal or photooxidation of alkenes (olefins) proceeds according to Schemes 3 and 4.

Scheme 3

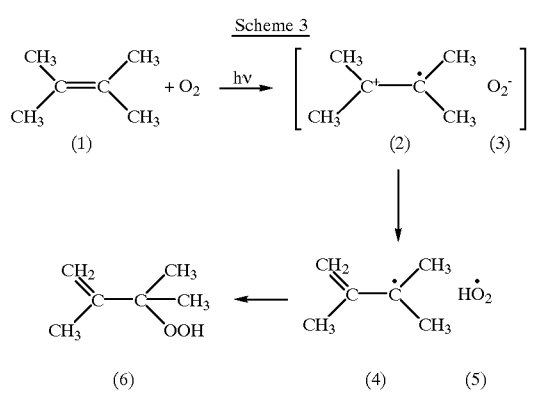

As seen in Scheme 3, the initial step of the proposed mechanism is proton transfer from 2,3-dimethyl-2-butene (1) to form the alkene radical cation (2) formed by photoexcitation, to $O_2^-$ (3). Radical cations of small olefins are spectroscopically established transients, and some have been previously observed in zeolites. Proton transfer from the radical cation (1) to $O_2^-$ is fast because of the high acidity of the cations. Efficient proton transfer quenching of the charge-transfer pair seems to be the main reason for the rather high quantum yields to reaction of the hydrocarbon photooxidations, typically between 0.1 and 0.3 because it furnishes a path that is competitive with back electron transfer. The allyl (4) and hydroperoxy radical (5) so produced undergo cage recombination to yield the observed alkyl hydroperoxide (6).

Thermal oxidation proceeds under appropriate conditions along the same lines through formation of the alkene radicals to form alkyl hydroperoxide.

Scheme 4 shows a process for selective alkene photooxidation in cation-exchanged zeolites Y or L for 2,3 dimethyl-2-butene (A), 2-butene (B) and propylene (C).

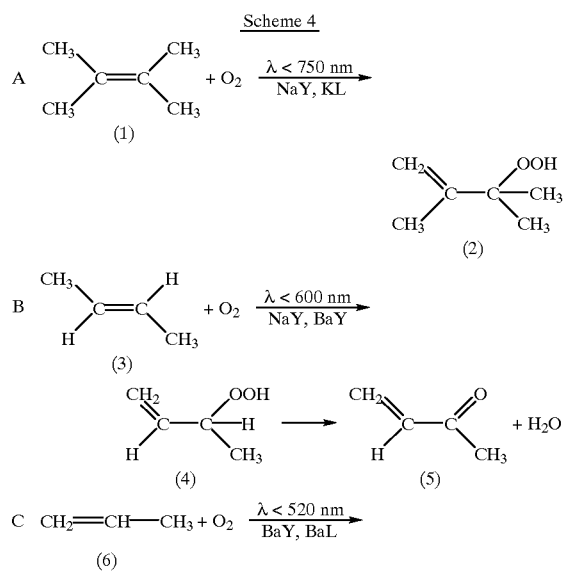

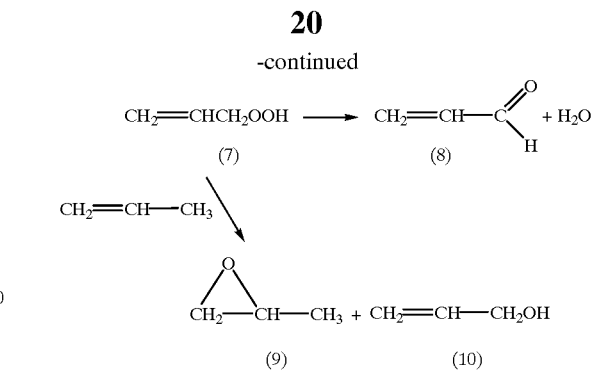

Visible light-induced oxidations of the above three alkenes by $O_2$ are displayed in Scheme 4. The reaction of 2,3-dimethyl-2-butene (DMB) into 2,3-dimethyl-3-hydroperoxy-1butene in alkali or alkaline-earth zeolites occurs at the fastest rate and is substantially the same as seen in general Scheme 3.

Scheme 4B shows conversion of 2-butene via the same route as seen in Scheme 4A through hydroperoxide intermediate (4) to compound acroleine (5).

Selected zeolite was zeolite Y in its $Na^+$ or $Ba^{2+}$-exchanged form. Studies were also conducted with K or Ba forms of zeolite L. Loading of a self-supporting pressed zeolite matrix of one-micron NaY crystallites (1 cm diameter, 50–100 micron thick) with 0.5 Torr DMB and 1 atm $O_2$ gas at ambient temperature resulted in presence of 1–2 hydrocarbons per supercage and one $O_2$ every 3–4 supercages on average. Exposure of the zeolite to visible or near-infrared light at wavelengths as long as 750 nm induced oxidation of the olefin. Oxidation was detected by in situ FT-infrared spectroscopy. An infrared spectrum of the product taken upon oxidation of >90% of the loaded 2,3-dimethyl-2-butene by visible light at 50° C. is shown in FIG. 9.

Figure 9:
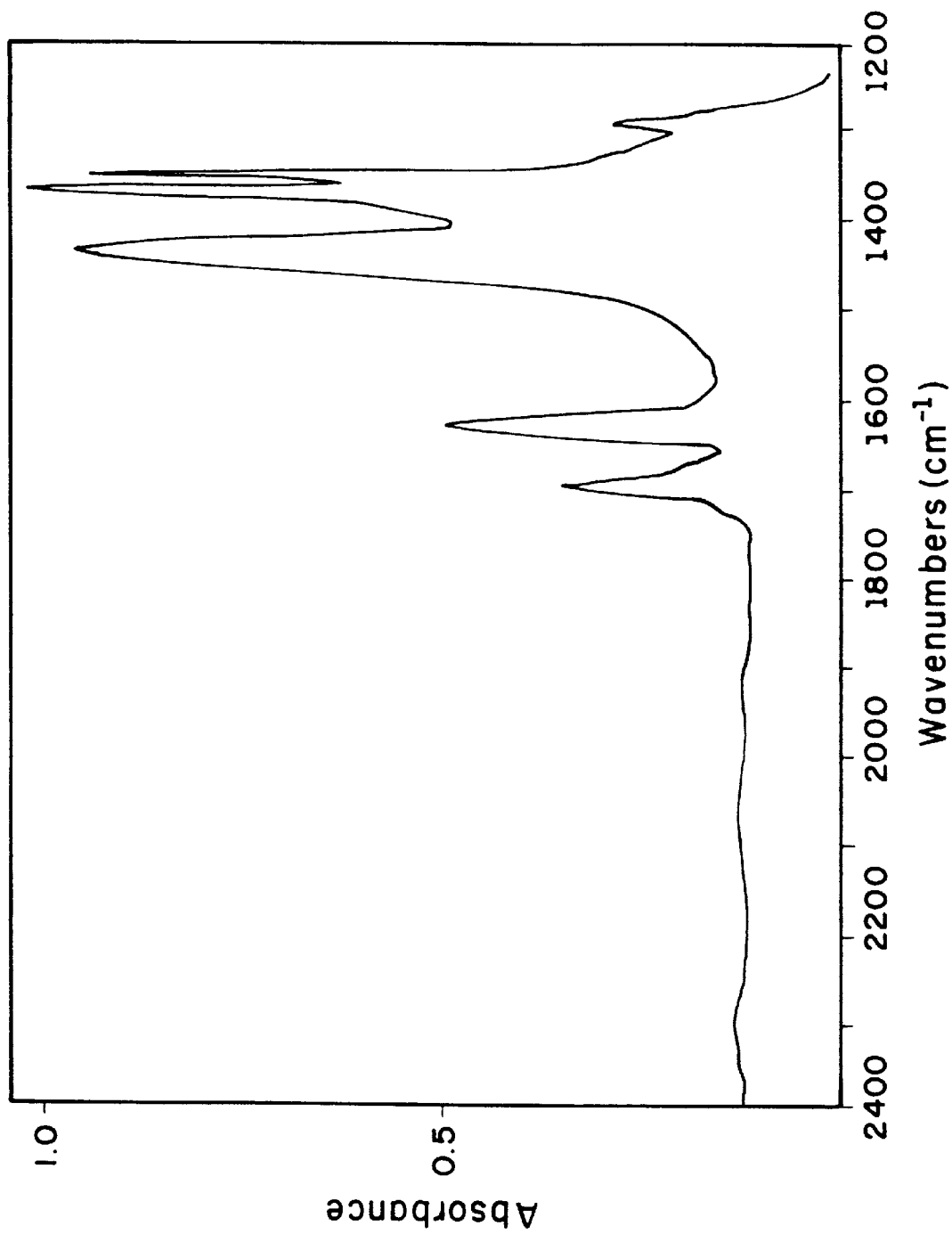
FIG. 9 is a graph depicting infrared product spectrum on conversion of 2,3-dimethyl-2-butene and $O_2$ in zeolite NaY under visible light.

FIG. 9 is an infrared product spectrum showing higher than 90% conversion of 2,3-dimethyl-2-butene and $O_2$ in zeolite NaY under visible light at –50° C. All absorptions originate from 2,3-dimethyl-3-hydroperoxide-1-butene except the band at 1708 cm$^{-1}$, which depicts production of about 2% acetone. For experiments below room temperature, the miniature infrared gas cell holding the zeolite pellet was mounted inside a variable-temperature vacuum system.

The spectrum seen in FIG. 9 is that of the corresponding alkene hydroperoxide (2,3-dimethyl-3-hydroperoxy-1-butene) plus a small amount of about 2% of acetone, the established thermal decomposition product of DMB alkene hydroperoxide. The same photooxidation was observed in zeolite BaY, KL, or BaL. Product and yield were independent of whether the visible output of a conventional tungsten lamp or the monochromatic emission of a continuous-wave visible laser was used for photolysis. Use of the laser was especially convenient for wavelength dependence studies.

Figure 10:
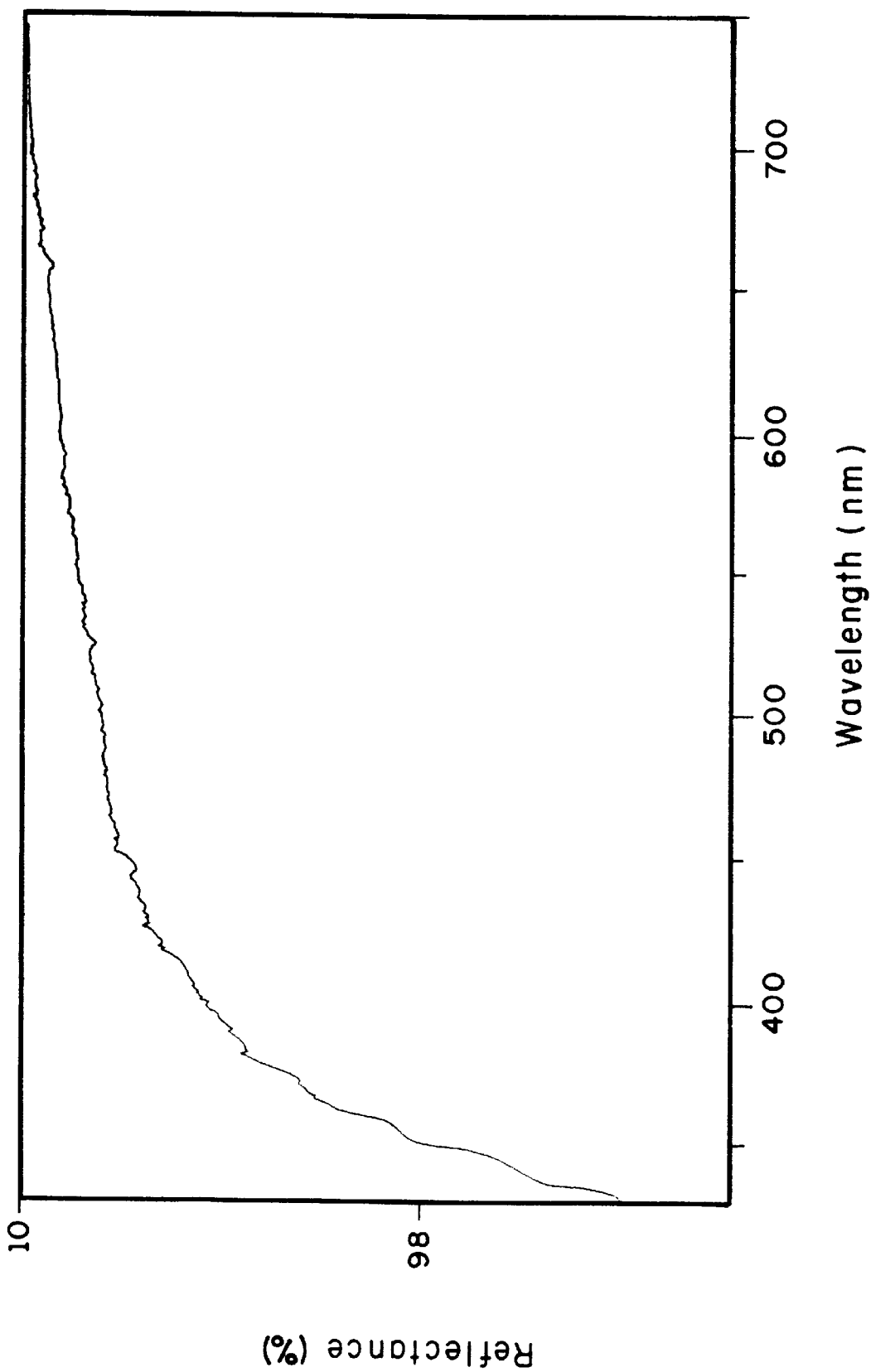
FIG. 10 is a graph depicting UV-visible reflectance spectrum of 2,3-dimethyl-2-butene and $O_2$ gas-loaded zeolite NaY at room temperature showing the alkene•$O_2$ charge-transfer absorption tail.

FIG. 10 depicts UV-visible reflectance spectrum of DMB and $O_2$ gas-loaded zeolite NaY at room temperature showing the alkene•$O_2$ charge-transfer absorption tail. FIG. 10 is a recording of an optical spectrum of the 2,3-dimethyl-2-butene and $O_2$-loaded NaY pellet that reveals a weak continuous absorption tail in the visible extending into the red spectral region. The spectrum appears only when both olefin and $O_2$ are present in the zeolite and therefore, originates from a hydrocarbon•$O_2$ collisional complex. This absorption is responsible for the light-induced oxidation of the olefin. The highly scattering nature of the pressed zeolite pellet in the UV-visible region required measurement of the optical spectrum in the reflectance mode with an integrating sphere. The steep increase of the absorption towards shorter wavelengths, especially at λ<400 nm is attributed to a longer path of the light due to increased scattering. Subsequently prepared optically transparent monolayers of large (40 micron) NaY crystals on a $CaF_2$ support showed sharply reduced scattering of these layers that allow recording of the true absorption profile, which features a shallow maximum between 400 and 500 nm.

The zeolite (cation) dependence of the absorption and the relationship between its onset and the ionization potential of the hydrocarbon indicate that the visible absorption is due to a hydrocarbon•$O_2$ contact charge-transfer transition. On absorption of a photon by an olefin•$O_2$ collisional complex, an electron is transferred from the hydrocarbon to oxygen, resulting in the formation of alkene radical cation and $O_2^-$. For 2,3-dimethyl-2-butene•$O_2$ in the liquid hydrocarbon or gas phase, the charge-transfer adsorption tail starts around 400 nm. According to FIG. 10, this implies a very large red shift of 350 nm for the olefin•$O_2$ adsorption in NaY, indicating a strong stabilization of the excited charge-transfer state by the zeolite cage.

Further seen in Scheme 4C is a partial oxidation of propylene. For this small alkene, selectivity is a particularly tough challenge. Irradiation of propylene (6) and $O_2$-loaded zeolite BaY at room temperature with green or blue light λ<520 nm induced partial oxidation of the olefin. The need for shorter wavelength photolysis light compared to 2,3-dimethyl-2-butene oxidation reflects the higher ionization potential of propylene (9.7 eV versus 8.3 eV). Readily identified products in Scheme 4C were acrolein (8), allyl hydroperoxide (7), and propylene oxide (9). The hydroperoxide was found to be stable when the zeolite was kept at a low temperature of −100° C. Photolysis experiments at this temperature allowed elucidation of the origin of aldehyde and epoxide product. Allyl hydroperoxide was the main product at −100° C., the remaining 13% were propylene oxide. Warm-up of the zeolite after photo-accumulation of the hydroperoxide (7) produced propylene oxide (9) if excess propylene was kept in the matrix, but produced only acrolein (8) if the olefin was removed prior to warm-up. Therefore, allyl hydroperoxide is the primary photoproduct and acrolein originates from dehydration of the hydroperoxide. Propylene oxide (9), on the other hand, is produced by thermal oxidation from allyl hydroperoxide to excess olefin. Thermal rearrangement of the hydroperoxide to acrolein exhibits a steep temperature dependence while the epoxidation reaction does not. The aldehyde (8) is therefore the preferred final oxidation product of the visible light-driven propylene oxidation at elevated zeolite temperature. For example, when conducting the propylene+$O_2$ photoreaction at 55° C., the acrolein to propylene oxide ratio is 2 to 1. Variation of the propylene loading level gives an additional handle on the acrolein/propylene oxide branching.

In another study both propylene and oxygen were loaded into zeolite BaY under a variety of pressure conditions while the matrix was held at −100° C. Pressures for propylene varied from 3 Torr (0.004 atm) to 10 Torr (0.013 atm), whereas pressures of oxygen varied from 400 Torr (0.53 atm) to 760 Torr (1 atm). The reactants were exposed to 488 nm light from either a CW Ar-ion laser or a filtered tungsten source. The major product was allyl hydroperoxide (AHP), which was formed with approximately 99.8% selectivity at greater than 30% conversion.

Upon warming of the zeolite matrix in the presence of excess propylene, one fraction of the allyl hydroperoxide decomposed to give acrolein and water, while the other fraction reacted with propylene to form allyl alcohol and propylene oxide. The final product distribution at room temperature was therefore acrolein, 37% selectivity; propylene oxide, 31% selectivity; and allyl alcohol, 31% selectivity.

When the same study was repeated at room temperature, the reaction yielded allyl hydroperoxide with 98% selectivity as the intermediate. In addition to allyl hydroperoxide, the final products included propylene oxide and acrolein (propenal), which were produced in approximately equal amounts. Overall selectivities for all the products were allyl hydroperoxide, 38%; propylene oxide, 36%; and acrolein, 24%. Conversions were as high as 50%.

The most important result of propylene photooxidation by visible light in zeolite is the unprecedented selectivity in terms of the allyl hydroperoxide intermediate, which at ambient temperature is higher than 98%. The selectivity is undiminished even upon consumption of 50% of the propylene loaded into the zeolite. On the basis of spectroscopy of the visible propylene•$O_2$ charge-transfer absorption and the measured infrared product growth, a rather high reaction quantum efficiency of 20% was found. Essentially identical results were obtained with this reaction in zeolite BaL.

In one study, dehydrated NaY was loaded with trans-2butene and oxygen at −50° C. Irradiation below 600 nm (514 nm, 400 mw cm$^2$) for 1 hour gave rise to 3-hydroperoxy-l-butene as the exclusive photooxidation product. Selectivity was greater than 99%, and overall conversion was greater than 30%. Photolysis could be conducted for up to 10 hours with no accompanying loss of selectivity. After photolysis, the hydroperoxide-containing zeolite was warmed up to room temperature. Upon warming, some thermal decomposition of 3hydroperoxy-l-butene was observed to also yield s-trans and s-cis conformers of methyl vinyl ketone.

Irradiation of cis-2-butene and $O_2$ loaded onto dehydrated NaY at −50° C. yielded 3-hydroperoxy-1-butene. The product was the same as that obtained when trans-2-butene above was used as the starting material. Selectivity (above 99%) and conversion (above 30%) were the same. Upon warming from −50° C. to 0° C., thermal reaction of the hydroperoxide-contained zeolite yielded methyl vinyl ketone, 3-hydroxy-l-butene and cis-2,3-epoxybutane. Removal of excess 2-butene starting material prior to warm-up of the hydroperoxybutene-loaded matrix resulted in the formation of only the methyl vinyl ketone, with no epoxide or alcohol.

Other alkenes were tested and similar selectivity of the thermal or photooxidation was observed.

C. Alkyl Substituted Benzenes

Oxidation of benzenes substituted with alkyl to benzaldehyde is commercially a very important process. Yet, there is currently no process that would oxidize toluene by $O_2$ to benzaldehyde selectively.

The current invention allows such selective oxidation of toluene to benzaldehyde.

The oxidation reaction of ethyl benzene is shown in Scheme 5.

Scheme 5

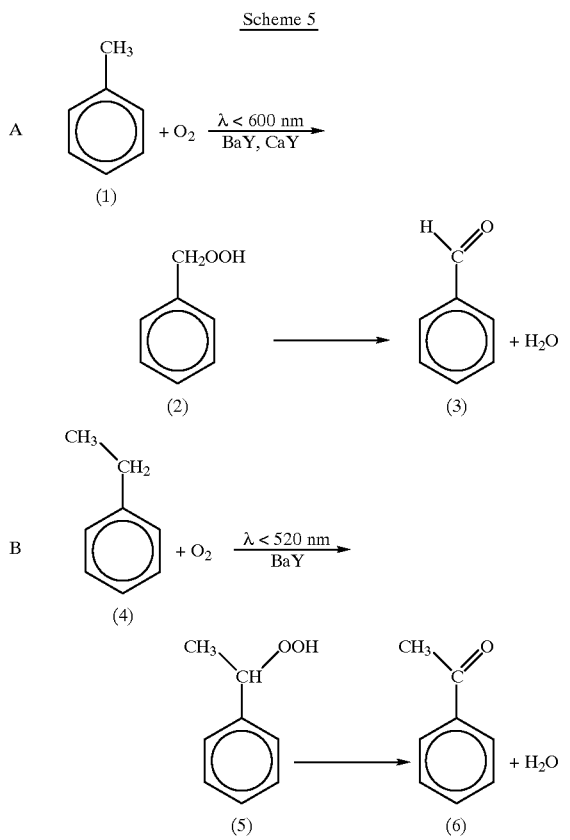

Using the photochemical and infrared probing techniques described above for the study of the visible light-induced alkene oxidations, it was discovered as seen in Scheme 5A that toluene (1) reacts with $O_2$ in zeolite BaY or CaY at $\lambda < 600$ nm to form benzaldehyde (3) and $H_2O$ without byproduct. When the photoreaction was run while the zeolite pellet was held at 60° C., benzyl hydroperoxide (2) was found to be trapped. Warm-up of the matrix to room temperature resulted in spontaneous dehydration to benzaldehyde, indicating that the hydroperoxide (2) is a reaction intermediate. Complete selectivity was sustained even upon conversion of as much as half of the toluene loaded into zeolite.

Scheme 5B shows conversion of ethylbenzene (4) to acetophenone (6) via formation of appropriate benzyl hydroperoxide (5).

Figure 11:
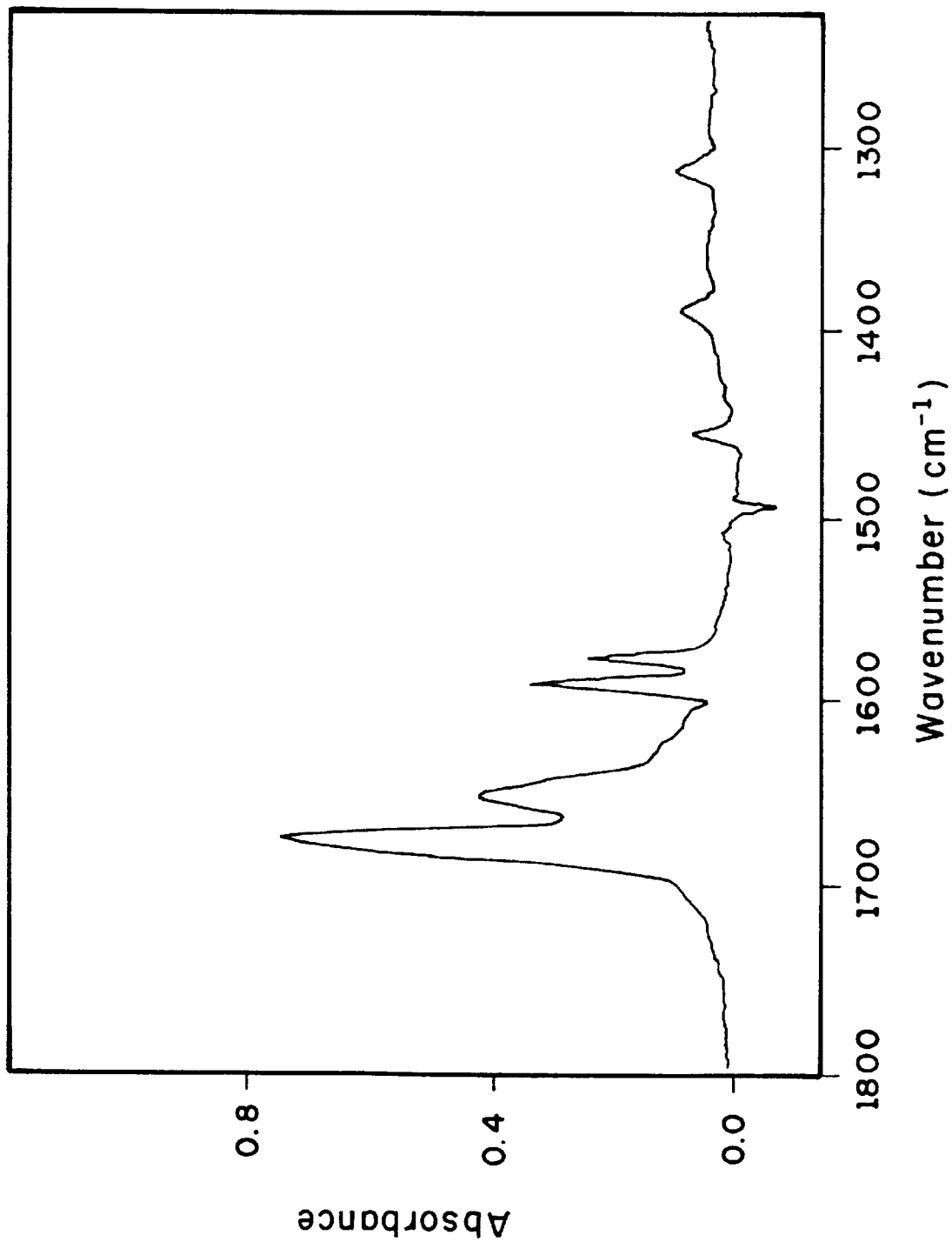
FIG. 11 is a graph showing infrared difference spectrum upon 30% conversion of toluene and $O_2$ in zeolite BaY with visible light at ambient temperature. Benzaldehyde and $H_2O$ are the only final oxidation products.

Conversion of toluene is further illustrated in FIG. 11. FIG. 11 shows an infrared difference spectrum upon 30% conversion of toluene and oxygen in zeolite BaY with visible light at ambient temperature.

As seen in FIG. 11, benzaldehyde and water are the only final oxidation products formed. No overoxidation of toluene to benzoic acid occurred. Such overoxidation is the main problem in Co(III) catalyzed autoxidation of toluene currently available. Overoxidation of benzaldehyde in the case of the visible light-driven reaction in the zeolite is prevented because the ionization potential of the aldehyde (9.5 eV) is higher than that of toluene (8.8 eV). Therefore, the benzaldehyde•$O_2$ charge-transfer absorption does not extend into visible region, making it inaccessible to photolysis light. As a result, no further oxidation to benzoic acid can occur.

In a similar study, partial oxidation of ethylbenzene to acetophenone was achieved in BaY with complete selectivity. The selectivity of these partial oxidations by $O_2$ is unprecedented.

In additional studies, isopropylbenzene, known as cumene and oxygen at 6080 Torr (8 atm) were loaded into BaY. Irradiation at 458 nm with 250 mW/cm$^2$ laser power for 2 hours resulted in the formation of cumene hydroperoxide, exclusively, with 40% conversion. Within the zeolite, cumene hydroperoxide decomposes into acetone and phenol by one pathway, and methanol and acetophenone via another pathway. The branching ratio between these two decomposition pathways was approximately one to one, and all four products were observed in every case. A ten-fold reaction increase was observed when the oxygen partial pressure was increased from 760 to 7,600 Torr (1 to 10 atm).

D. Thermal and Photooxidation of Cyclic Hydrocarbons

Oxidation of cyclic hydrocarbons, such as cyclohexane, is very important for the chemical industry. As above, up to date there is no available suitable process for selective oxidation of cyclohexane and other cyclic hydrocarbons.

Thermal or photooxidation according to the invention proceeds according to Scheme 6.

Scheme 6

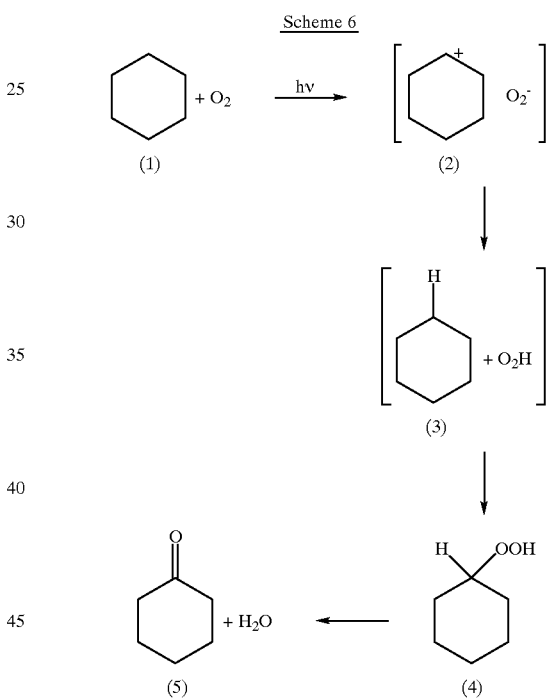

In Scheme 6, the initial step following excitation of the charge-transfer state is proton transfer from the cyclohexane (1) radical cation to $O_2$—. Cyclohexane radical cation (2) is a spectroscopically established transient with a lifetime of just 300 ps with respect to deprotonation in the neat liquid at room temperature. The main reason for the rather high quantum yield of the reaction is an efficient proton transfer quenching of the charge-transfer pair. Cyclohexyl and hydroperoxy radicals (3) so produced undergo cage recombination to yield the observed cyclohexyl hydroperoxide (4) which is further converted to cyclohexanone (5).

Figure 12:
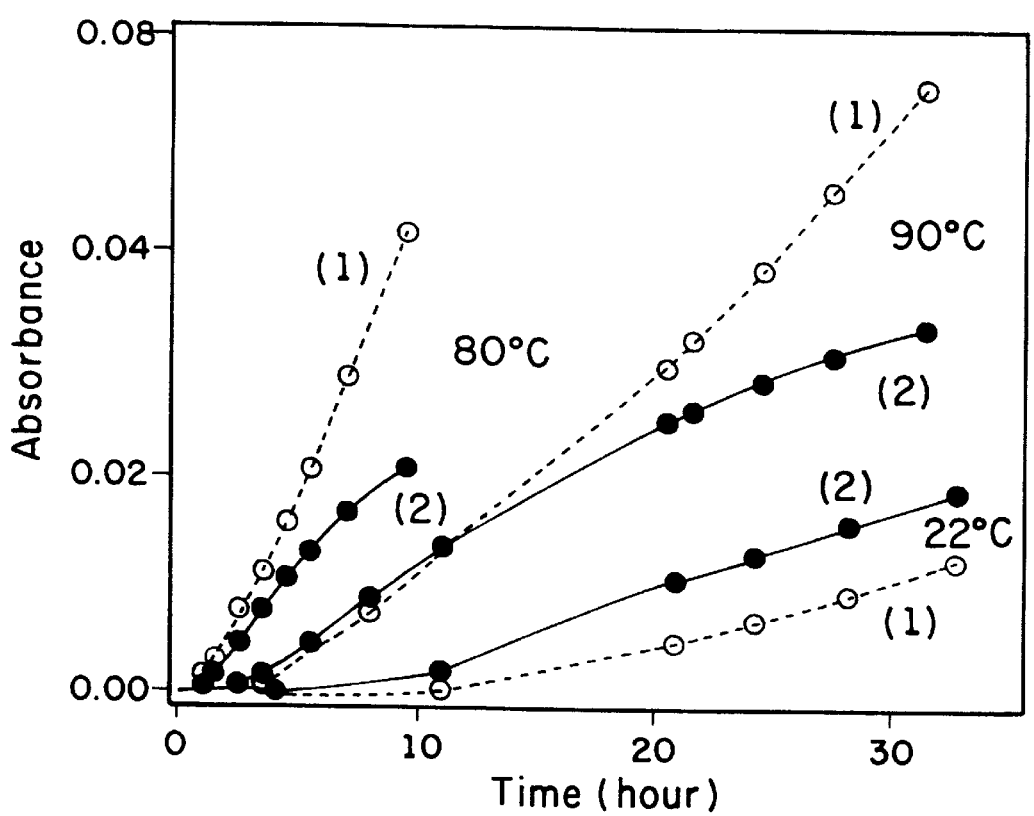
FIG. 12 is a graph showing absorbance growth kinetics of the 1705-$cm^{-1}$ cyclohexanone band and the 1367-$cm^{-1}$ cyclohexyl hydroperoxide absorption upon 458- and 514-nm photolysis at room temperature.

Cyclohexyl hydroperoxide rearranges to cyclohexanone in a slow thermal process, the non-zero slope of the cyclohexanone (5) growth curve indicates, as seen in FIG. 12, that some of the ketone emerges concurrently with cyclohexyl hydroperoxide as well.

Figure 14A:
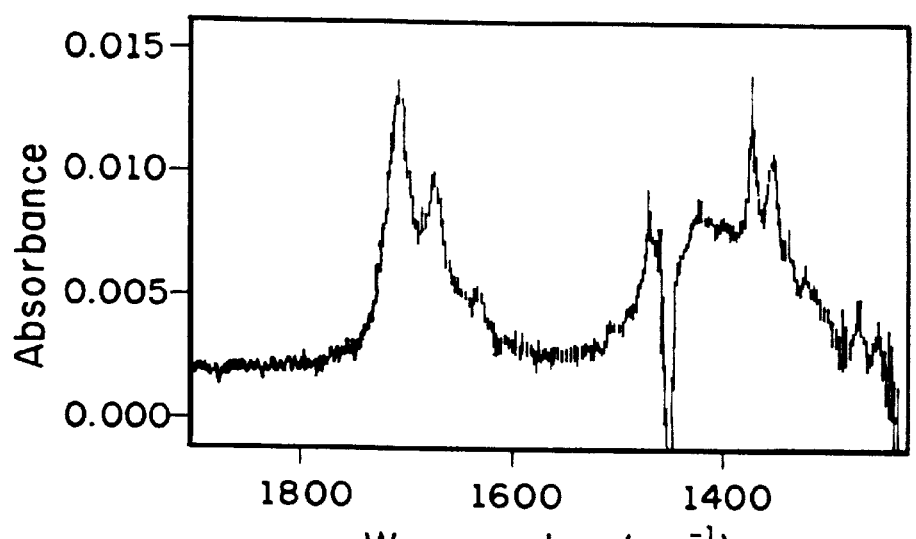
FIG. 14A shows infrared spectrum cyclohexane and oxygen before and after photolysis at 458 nm.

Photooxidation of cyclohexane into cyclohexanone was studied in experiments where cyclohexane was loaded into NaY. Results are seen in FIG. 14. Infrared bands were observed at 2932, 2851, 1452, 905, and 861 cm$^{-1}$. Subsequent addition of 500 Torr of $O_2$ did not result in any notable spectral changes. Chemical reaction was observed when irradiating the room temperature zeolite matrix with green or blue light (514, 488, or 458 nm emission of an Ar-ion laser), but no spectral changes were noticed when shinning light on a zeolite pellet that contained either only cyclohexane or oxygen. An infrared difference spectrum following 120 min of photolysis at 458 nm (200 mW cm$^{-2}$) is displayed in FIG. 14A.

Figure 14B:
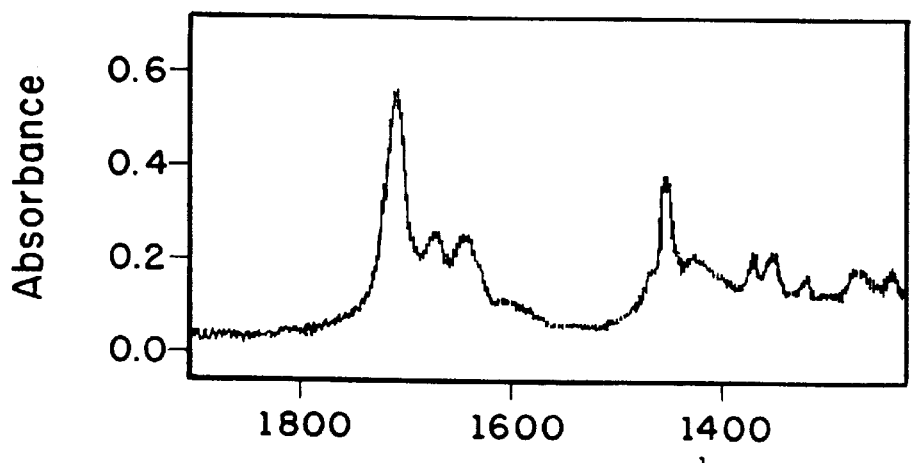
FIG. 14B shows prolonged irradiation of a cyclohexane and $O_2$ loaded NaY at 488 nm.
Figure 14C:
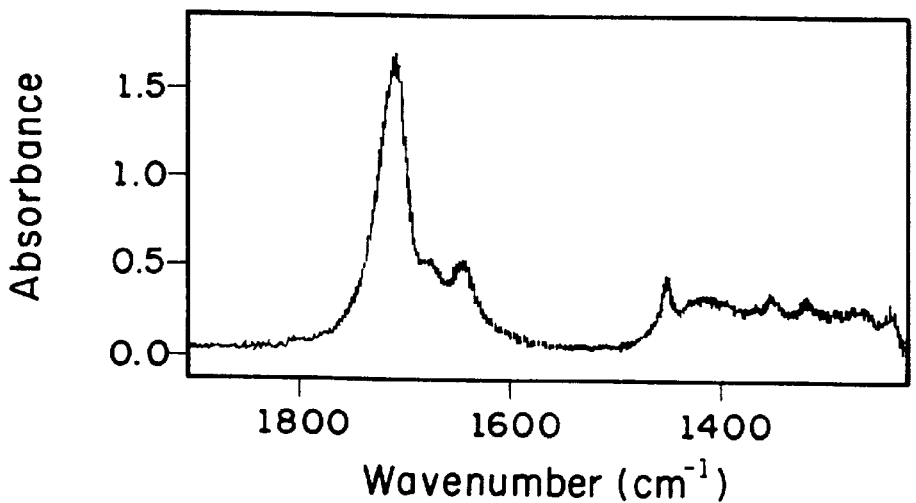
FIG. 14C shows irradiation of an HCl-pretreated NaY loaded with cyclohexane and $O_2$ for 5 h at 488 nm.

Graphs in FIG. 14 show infrared difference spectrum of the NaY pellet loaded with cyclohexane and $O_2$ before and after Argon-iron laser photolysis. FIG. 14A shows infrared spectrum of the NaY pellet loaded with cyclohexane and oxygen before and after photolysis at 458 nm (2 h, 200 mW cm$^{-2}$) at room temperature. FIG. 14B shows prolonged irradiation of a cyclohexane and $O_2$ loaded pellet NaY at 488 rm. The product growth corresponds to reaction of 35% of the cyclohexane loaded into the zeolite. The trace shows the reaction products only (difference between spectra before loading of the pellet and after photolysis and pumping off of excess $C_6H_{12}$). FIG. 14C shows irradiation of an HCl-pretreated NaY pellet loaded with cyclohexane and $O_2$ (750 Torr) for 5 h at 488 nm (500 mW cm$^{-2}$). Seventy-one percent of the cyclohexane has been converted. The trace shows the difference between spectra before loading of the pellet and after irradiation and pumping off of the excess reactants.

The negative features show the consumption of cyclohexane, while the positive bands originate from photoproducts. Recording of infrared spectra of authentic samples of cyclohexyl hydroperoxide, cyclohexanone, and $H_2O$ in zeolite NaY confirmed that photolysis product absorptions originate from these three species. No unassigned product band remained. Specifically, no infrared band of cyclohexanol was observed. A lower limit of 50 for the cyclohexanone to cyclohexanol branching ratio was calculated. Infrared frequencies of photoproducts and of authentic samples are presented in Table 1.

TABLE 1

Absorption Frequencies of Cyclohexyl and Its Oxidation Reaction Products
Authentic samples[a]

| reaction product | cyclohexyl hydroperoxide | cyclohexanone | water |
|---|---|---|---|
| 3400[b] | | | 3400 |
| 3200 | 3200 | | |
| 2941 | 2941 | 2937 | |
| 2861 | 2859 | 2863 | |
| 1705 | | 1705 | |
| 1670 | | 1674 | |
| 1644 | | | 1643 |
| 1468 | 1469 | 1464 | |
| 1454[c] | 1453 | 1451 | |
| | | 1426 | |
| | | 1420 | |
| 1413[d] | 1411[d] | | |
| 1367 | 1367 | | |
| | | 1350 | |
| 1346 | 1346 | 1342 | |
| 1313 | | 1313 | |
| | 1301 | | |
| 1267 | | 1268 | |
| 1259 | 1259 | | |
| 1230 | | 1229 | |
| 908[c] | | 907 | |
| 900 | 900 | | |
| 892 | 893 | | |
| 863[c] | 865 | 862 | |
| 838 | 838 | | |

[a]All product absorptions are assigned except for a weak band at 1330 cm$^{-1}$ whose intensity as not reproducible from one experiment to another.
[b]Very broad, fwhm ≈ 200 cm$^{-1}$.
[c]Overlapped by decreasing cyclohexane band.
[d]Broad.

Table 1 lists absorption frequencies of cyclohexyl hydroperoxide and its oxidation reaction products in authentic samples in NaY zeolite, expressed in cm$^{-1}$.

Since authentic spectra of cyclohexyl hydroperoxide loaded into NaY showed traces of cyclohexanone, the hydroperoxide spectrum was also recorded in $CD_3CN$ solution. There was excellent agreement between the spectra in the two media. An exception is the ν(OH) mode which is red shifted in the zeolite by 200 cm$^{-1}$ due to strong H bonding. Cyclohexyl hydroperoxide, cyclohexanone, and $H_2O$ are the exclusive products of visible light-induced oxidation of cyclohexane by $O_2$ in zeolite NaY. This holds even upon conversion of as much as 35% of the cyclohexane loaded into the zeolite, as shown in FIG. 14B.

Cyclohexyl hydroperoxide was also found to rearrange thermally to cyclohexanone without side reaction. This process is readily observed by infrared difference spectroscopy when keeping a hydroperoxide-loaded NaY matrix in the dark at room temperature. It is strongly accelerated in acid (HCl) treated NaY. FIG. 14C shows the infrared product spectrum upon blue light-induced oxidation of cyclohexane (488 nm, 500 mW cm$^{-2}$) in an HCl pretreated zeolite for 5 hours. Comparison with FIG. 14A, where the hydroperoxide to cyclohexanone ratio is about 4:1, shows that even the most intense cyclohexyl hydroperoxide band at 1367 cm$^{-1}$ is barely visible in spectrum 14C. Thermal rearrangement of cyclohexyl hydroperoxide to cyclohexanone and water is an established intramolecular heterolytic reaction in acidic solution.

Infrared spectra like the one shown in FIG. 14 constitute direct proof that the products are generated in the interior of the NaY particles rather than on their outer surface. If one exposes cyclohexanone at a fixed gas pressure to a pellet of zeolite NaY and a pellet of NaA particles, a strong infrared spectrum is observed in NaY while only extremely weak features appear in the case of NaA. Type Y and type A zeolites both have a three-dimensional network of α-cages of similar size, but the window openings of NaA are too small (4 Å) to permit diffusion of cyclohexanone into the zeolite. Therefore, adsorption can occur only at the outer surface. By contrast, the window openings of zeolite Y α-cages have a diameter of 7 Å, hence cyclohexanone can readily diffuse into the zeolite particles. The infrared product absorptions shown in spectra originate exclusively from molecules that reside inside the zeolite crystallites.

Figure 13:
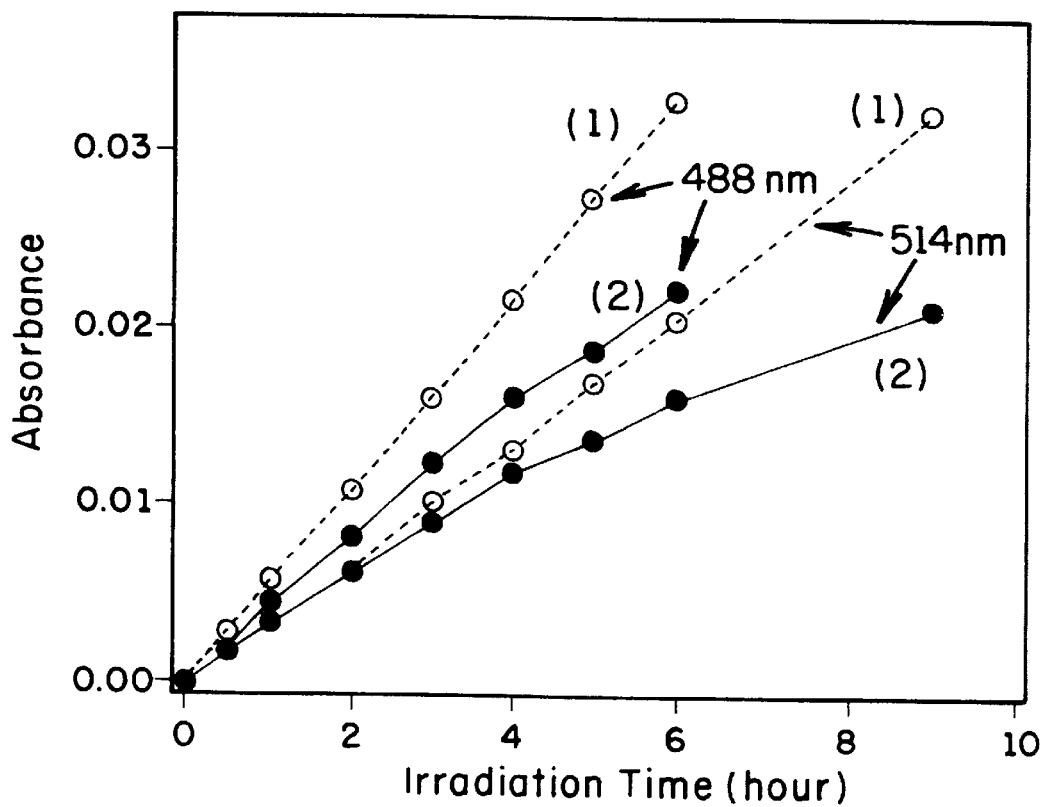
FIG. 13 is a graph showing absorbance growth kinetics of the 1705$cm^{-1}$ cyclohexanone band (curve 1) and the 1367-$cm^{-1}$ cyclohexyl hydroperoxide absorption (curve 2) upon thermal reaction at 22, 50, and 80° C. The size of the circles indicates the peak-to-peak noise.

The growth kinetics of the products at two photolysis wavelengths, 514 and 458 nm, is displayed in FIG. 13. FIG. 13 are graphs showing infrared difference spectrum of the NaY pellet loaded with cyclohexane and $O_2$ before and after Argon-iron laser photolysis. The plot shows the infrared absorbance growth of the ν(C=O) mode of cyclohexanone at 1705 cm$^{-1}$ (curve 1) and of the $CH_2$ bending mode of cyclohexyl hydroperoxide at 1367 cm$^{-1}$ (curve 2). The extinction coefficient ratio of the cyclohexanone doublet at 1705/1670 cm$^{-1}$ and the hydroperoxide absorption at 1367 cm$^{31}$ $^{1}$ was determined to be 62.

According to the two growth curves, the cyclohexanone to hydroperoxide branching ratio is around 0.1 at the start of photolysis. While the hydroperoxide curve is heading toward an asymptotic limit, the cyclohexanone growth clearly accelerates with increasing photolysis time. Comparison of the 514- and 458-nm photolysis curves shows that the cyclohexanone to cyclohexyl hydroperoxide ratio increases somewhat at higher photon energies.

The quantum yield for reaction was calculated as the product growth per absorbed photon. In one typical photolysis experiment at 458 nm, the absorption of cyclohexane•O$_2$ at that wavelength was 0.04%. The incident photon flux corresponded to 8.3×10$^{-3}$ mol photons (hence 3.3×10$^{-6}$ mol photons absorbed by the C$_6$H$_{12}$•O$_2$ pairs) over an irradiation period in which the infrared absorbance growth was 0.016 at 1705 cm$^{-1}$ (cyclohexanone) and 0.012 at 1367 cm$^{-1}$ (cyclohexyl hydroperoxide). Taking into account the extinction coefficient of the absorptions, a total product growth of 1.0 ×10$^{-7}$ mol was calculated for the 3.3×10$^{-6}$ mol of 458-nm photons absorbed. Hence, the quantum yield to reaction is 0.03. This efficiency may be off by as much as a factor of 3 due to the large uncertainty in the absorption at 458 nm as estimated from the diffuse reflectance spectrum. The photooxidation of cyclohexane and O$_2$ on a variety of zeolites with blue and green light gave cyclohexyl hydroperoxide as the primary product. The zeolites used were BaY and NaY. At −50° C., cyclohexyl hydroperoxide could be generated by continuous irradiation with blue light. At room temperature irradiation with blue or green light, the hydroperoxide appeared to be more stable in NaY than BaY. The selectivity for cyclohexyl hydroperoxide was 100% at conversions greater than 70%.

Additionally to photooxidation, thermal oxidation of cyclohexane into cyclohexanone was discovered. When keeping a cyclohexane and O$_2$-loaded NaY matrix in the dark at room temperature for 10 hours, a very small growth of cyclohexyl hydroperoxide was noticed. After about 20 hours, cyclohexanone growth was observed as well. An experiment with $^{18}$O$_2$ gave exclusively cyclohexanone-$^{18}$O, which confirms that no lattice oxygens are involved in the reaction. The kinetics of the reaction at room temperature is shown in FIG. 12.

FIG. 12 is a graph showing absorbance growth kinetics of the 1705-cm$^{-1}$ cyclohexanone band (curve 1) and the 1367-cm$^{-1}$ cyclohexyl hydroperoxide absorption (curve 2) at 20, 50 and 80° C. temperature. The size of the circles indicates the peak-to-peak. noise. While this thermal reaction is barely noticeable at 22° C., rates increase steadily with temperature. Curves corresponding to thermal reaction at 50 and 80° C. are also displayed in FIG. 12. At temperatures up to 80° C., no products other than cyclohexyl hydroperoxide, cyclohexanone, and water are observed. The slightly increased rates of the ketone growth at long times signal, again, a slow hydroperoxide to cyclohexanone interconversion.

Comparison of the product growth curves upon thermal (FIG. 12) and photochemical oxidation of cyclohexane (FIG. 13) shows that these two reaction types can easily be distinguished on the basis of the kinetics. At all temperatures the thermal reaction has an induction period with zero slope at the start of reaction while the photochemical curves do not.

The heating effect which accompanies laser irradiation of the zeolite is far too small to account for the observed photochemical rates.

With each of the different zeolites used, thermal autoxidation of cyclohexane to cyclohexyl hydroperoxide was found to take place, even at room temperature. The product of the photochemical reaction as well as the thermal reaction was therefore the same. However, visible light irradiation of the thermal reactant system enhanced the reaction rate by approximately a factor of ten. Decomposition of cyclohexyl hydroperoxide into cyclohexanone was observed to take place in all zeolites used. The rate of decomposition was found to decrease in the order of CaY>BaY>NaY.

UTILITY

Novel process for selective thermal or photooxidation of hydrocarbons is useful for the production of bulk and fine chemicals. The process is environmentally benign and an energy efficient alternative to currently used nonselective hydrocarbon autoxidation processes used for the manufacture of organic building blocks for plastics and synthetic fibers or as industrial intermediates in the manufacture of fine chemicals and industrial intermediates. The novel process does not generate any byproducts even at high a conversion rate of hydrocarbon.

In addition, the current process, particularly the thermal conversion, is also suitable for degradation of hydrocarbons, such as for example for remediation od contaminated aquifers, or for use in catalytic converters to remove the hydrocarbons from car or pane exhausts.

EXAMPLES

The current invention is illustrated in the following specific examples which describe both general and specific procedures utilized in the preparation of various compounds by the selective photooxidation of hydrocarbons in zeolites by oxygen. These Examples are illustrative only of the present invention and in no way are intended to limit the scope of the invention.

Unless indicated otherwise, all "percentages" given are expressed in terms of weight percent. "Photochemical conversions" are expressed in terms of the percent of reactant molecules exposed to light. "Thermal conversions" are expressed in terms of the percent of total reactant that was initially loaded into the zeolite.

Example 1

Preparation of Zeolites

This example describes the procedure for preparation of zeolites for loading with hydrocarbons.

Zeolite NaY as product LZ-Y52, obtained from Aldrich Chemical Co. Lot No. 03319TX, was pressed into self-supporting wafers of 12 mm diameter and a typical weight of 8 mg. The zeolite pellets were mounted inside a home-built miniature stainless steel cell. Prior to loading a hydrocarbon and O$_2$ from the gas phase, the zeolite pellet was dehydrated at 200° C. in the high-vacuum cell for 10–12 hours. A turbomolecular pump Model Varian V-60 (Varian, Palo Alto, Calif.) was used for evacuation during heating. All UV-visible light (UV-vis) measurements were conducted at ambient temperature (21° C.).

In one series of experiments the zeolite pellet was pretreated with a small amount of HCl. The gas was prepared on a vacuum line by the reaction of concentrated H$_2$SO$_4$ with dry NaCl powder. The dehydrated zeolite was heated to 200° C. and exposed to 0.6 Torr of the distilled HCl for 10 min. Thereafter, the pellet was evacuated at that temperature for 6 hours.

UV-vis spectra were obtained by diffuse reflectance measurements using a Shimadzu Model 2100 instrument with an integrating sphere set-up Model ISR-260 obtained from (VIDE).

For monitoring of photochemical reactions, hydrocarbon and $O_2$ gas were loaded into a dehydrated zeolite pellet inside a miniature vacuum cell equipped with KBr windows. The chemistry was followed in situ by FT-infrared spectroscopy using a Bruker Model IFS 113 or an IBM-Bruker Model IR 44 spectrometer obtained from IBM, Armonk, N.Y. Zeolite NaY is transparent in the infrared except for the region between 1200 and 920 $cm^{-1}$, and below 800 $cm^{-1}$. Photolysis was conducted with the emission of a prism-tuned continuous-wave Ar-ion laser (Coherent Model Innova 90-5 or 90-6, Coherent, Palo Alto, Calif.). The laser beam was expanded to the full size of the pellet. For experiments above or below room temperature, the infrared cell was mounted inside a variable-temperature Oxford cryostat Model DN1714.

For determination of the product ratio of monoxidated to oxidated hydrocarbon, the extinction coefficient ratio of the two molecules was estimated by recording infrared spectra upon thermal conversion. Following photoaccumulation of oxidated hydrocarbon, the excess monoxidated and $O_2$ were pumped off and the zeolite temperature was raised to 100° C. for several hours. The difference spectrum of the conversion, accelerated by the high temperature, allowed determination of the relative integrated intensities of oxidated hydrocarbon and the monoxidated hydrocarbon with an accuracy of 10%. Infrared spectra were calibrated for oxidated yields by manometric measurement of the uptake of the molecule from the gas phase.

Zeolite for large thermal or photooxidation conversion are prepared essentially in the same manner. Na ions may be exchanged for Ba or Ca ions.

Example 2
Residual Water in Zeolite

This example describes studies performed to determine whether photochemical or thermal oxidation are sensitive to the concentration of residual water in zeolite.

A series of experiments was conducted to determine the concentration of remaining $H_2O$ in BaY or CaY pellets after a typical dehydration procedure. An ideal infrared absorption of water for these measurements is the relatively narrow and moderately intense bending mode at 1640 $cm^-$. In order to determine the extinction of coefficient of this band, small, known amounts of water vapor (measured by manometric techniques) were absorbed into the dehydrated zeolite and infrared spectra recorded. The weight of the pellet was obtained by transferring it after the infrared measurement into a closed glass container of 100% humidity. Leaving the pellet for several days in this environment assured complete hydration. The weight of the dry pellet was calculated from that of the hydrated zeolite by assuming 26% water content (by weight). From these data and from the known density of supercages in zeolite Y ($3.8\times10^{20}g^{-1}$), previously described in *Zeolite Molecular Sieves: Structure, Chemistry and Use*, D. W. Breck, Wile, N.Y., (1974), the number of $H_2O$ molecules per supercage was calculated. Results were close to those reported for the extinction coefficient of the $H_2O$ infrared bending mode in zeolite NaY reported in *J. Phys. Chem.*, 67:1621 (1963).

A loading level of 0.3 $H_2O$ molecules per supercage of BaY or CaY following the standard treatment of 10 hours dehydration at 200° C. under high vacuum was found.

Example 3
Selective Thermal Oxidation of Hydrocarbons

This example describes general conditions used for selective thermal oxidation of hydrocarbons.

Hydrocarbons and oxygen are loaded into the zeolite matrix, or pellet, used for experimental purposes according to Example 1. Hydrocarbons and oxygen are loaded under several hundreds Torr pressure. Quantities absorbed were measured manometrically. Loaded hydrocarbon and oxygen are let to react at various temperatures from about 20° C. to about 150° C. for 30 minutes to several days at darkness. The progress of the thermal reaction is followed by observation of infrared spectrum. At room temperature and at several hundred Torr of hydrocarbon, the gas phase hydrocarbon in the miniature cell contributes significantly to the observed infrared spectrum. The gas phase bands are removed by spectral subtraction and the infrared extinction coefficient of the hydrocarbons is measured by lowering the pellet temperature to about −100° C. Extinction coefficients of infrared bands of formed oxidative product are determined from difference spectra interconversion of the hydroperoxide recorded upon thermal intermediate to the formed product and water.

Example 4
Selective Photooxidation of Hydrocarbon

This example describes general conditions used for selective thermal photooxidation of hydrocarbons.

Hydrocarbon is loaded from the gas phase into a dehydrated zeolite matrix prepared according to Example 1 at about −50° C. (negative 50° C.). Light irradiation is carried out by photolysis at 633 nm using a 300 mW $cm^{-2}$ light source with $3.5\times10^{21}$ photons at temperatures ranging from about −50° C. to about 30° C. for two or more hours. During the successful photooxidation all absorption bands for hydrocarbon decrease.

Products obtained by photooxidation are analyzed qualitatively and quantatively for the product formation selectivity.

Example 5
Thermal and Photooxidation Oxidation of Alkanes

This example describes general procedures used for thermal and photooxidation of alkanes.

Zeolite BaY and CaY were prepared by repeated ion exchange of NaY (LZ-Y52, Aldrich Lot. No. 04724PZ) at 90° C. in a 0.5 M solution of $BaCl_2$ or $CaCl_2$ according to Example 1. Ion exchange was 97% in the case of BaY and 98% for CaY as determined by ICP. Self-supporting wafers of 8mg of these materials were mounted inside a miniature vacuum cell that allowed in situ infrared monitoring of the reaction (FT-infrared spectrometer IBM-Bruker Model IR-44). The wafers were dehydrated at 200° C. under vacuum (Varian Model V-70 turbomolecular pump) for about 10 h before loading of alkane and $O_2$ from the gas phase. The miniature vacuum cell was mounted inside a variable temperature vacuum system with a tuning range from 77K to 200° C. (Oxford Model DN1714). The loading, level of alkane and $O_2$ was controlled by gas pressure and zeolite temperature.

For photolysis, a prism-tuned Ar-ion laser Coherent Model Innova 90-5 or a conventional tungsten lamp was used. The emission of the lamp was limited to the visible by a UV cutoff filter.

For thermal oxidation, loaded alkane is left to react in darkness for 3–5 days.

Example 6
Thermal and Photooxidation Oxidation of Propanes

This example describes general procedures used for thermal and photooxidation of propanes.

Zeolite BaY and CaY were prepared by repeated ion exchange of NaY (LZ-Y52, Aldrich Lot. No. 04724PZ) at 90° C. in a 0.5 M solution of $BaCl_2$ or $CaCl_2$ according to Example 1. Ion exchange was 97% in the case of BaY and 98% for CaY as determined by ICP. Self-supporting wafers of 8mg of these materials were mounted inside a miniature vacuum cell that allowed in situ infrared monitoring of the reaction (FT-infrared spectrometer IBM-Bruker Model IR-44). The wafers were dehydrated at 200° C. under vacuum (Varian Model V-70 turbomolecular pump) for about 10 h before loading of propane and $O_2$ from the gas phase. The miniature vacuum cell was mounted inside a variable temperature vacuum system with a tuning range from 77K to 200° C. (Oxford Model DN1714). The loading level of propane and $O_2$ was controlled by gas pressure and zeolite temperature.

For photolysis, a prism-tuned Ar-ion laser Coherent Model Innova 90-5 or a conventional tungsten lamp was used. The emission of the lamp was limited to the visible by a UV cutoff filter.

For thermal oxidation, loaded propane is left to react in darkness for 3–5 days.

Example 7
Thermal or Photooxidation of alkane 2,3-Dimethyl-2-Butene

This example describes the process for thermal photooxidation of alkene 2,3-dimethyl-2-butene into 2,3-dimethyl-3-hydroperoxy-1-butene.

Photooxidation 2,3-dimethyl-2-butene (DMB) in an amount of 10 $\mu$mol/ 10 mg zeolite structure was loaded from the gas phase into a dehydrated NaY zeolite wafer prepared according to Example 1 at –50° C. (negative 50° C.). Irradiation was carried out by photolysis at 633 nm using a 300 mW cm$^{-2}$ light source with 3.5 ×10$^{21}$ photons at temperatures ranging from about –50° C. to about 30° C. for two hours, during which time all absorption bands for DMB decreased.

Thermal Oxidation

The same procedure for loading DMB into zeolite was used as for photooxidation above, except that instead of irradiation with light, the loaded matrix was kept in the dark at room temperature, at +50° C. and at +80° C. for 10 hours.

Products obtained by photooxidation or by thermal oxidation were analyzed qualitatively and quantatively for the product formation selectivity. Results are described above and seen in FIGS. 9 and 10.

Using the same procedure as described for photooxidation, photolysis was carried out at 514 nm or 458 nm for 30 minutes at –50° C. using a 400 mW cm$^2$ light source.

Example 8
Thermal or Photooxidation of Toluene

This example describes the process for thermal or photooxidation of toluene into benzaldehyde.

Toluene was loaded from the gas phase into a sample of dehydrated zeolite BaY, which was prepared by ion exchange of NaY in a 0.5 M $BaCl_2$ solution according to Example 1. Inductively-coupled plasma atomic emission spectroscopy showed that 95% of the Na$^+$ ions had been replaced by Ba$^{2+}$. Oxygen was then introduced into the matrix at 500 Torr (approximately 0.66 atm), as described in Example 1.

Photooxidation

Several visible light sources were used similar to Example 3 to initiate photooxidation of the toluene•$O_2$ complex at ambient or other temperatures from as low as –50° C. to a high of 80° C. A tungsten source (wavelengths greater than 390 nm) with a Corning filter No. 3-75 as well as blue or green emissions from a continuous wave (CW) dye laser or an argon (Ar-ion) laser were used to produce light at 400 mW/cm$_2$ power. Upon irradiation for three hours, the oxidation product benzaldehyde was identified as the exclusive final oxidation product.

In one variation of the process, the oxygen partial pressure was increased from 500 Torr (0.66 atm) to 4000 Torr (8 atm). Such increase of pressure enhanced the reaction rate by a factor of approximately 5.

Another variation in toluene and oxygen were supported on dehydrated zeolite CaY instead of the BaY. Preparation of the CaY was carried out according to Example 1, with ion exchange of NaY carried out in a 0.5 M $CaCl_2$ solution. Subsequent analysis of the CaY revealed that 98% of the Na$^+$ sites had been replaced by Ca$^2$+. Photooxidation of the toluene•$O_2$ zeolite moiety was initiated by visible light at wavelengths below 590 nm. At room temperature, selectivity was 100% at more than 50% conversion. Benzaldehyde was the only product isolated.

Thermal Oxidation

Toluene and oxygen are loaded into the zeolite matrix according to Example 1. Hydrocarbons are loaded under several hundreds Torr pressure. Quantities absorbed are measured manometrically. Loaded toluene and oxygen are let to react at various temperatures from about 20° C. to about 150° C. for three days at darkness. The progress of the thermal reaction is followed by observation of infrared spectrum. At room temperature and several hundred Torr of toluene, toluene is thermally converted to benzaldehyde.

Example 9
Thermal and Photooxidation of Olefins

This example describes studies to determine selectivity of thermal or photooxidation of olefins.

Zeolite NaY or BaY, KL or BaL matrix was prepared as in Example 1. Self-supporting pressed zeolite matrix of one-micron NaY crystallites of about 1 cm diameter, 50–100$\mu$ thick was loaded with 0.5 Torr olefin and 1 atm $O_2$ gas at ambient temperature resulting on average in 1–2 hydrocarbons per supercage and one $O_2$ molecule per 3–4 supercages. Tested olefins were 2,3-dimethyl-2-butene and propylene.

Photooxidation

For photooxidation conversion, the loaded zeolite matrix was exposed to visible or near-infrared light at wavelengths as long as 750 nm for ten hours. Such induced oxidation of the olefins was detected by in situ FT-infrared spectroscopy. Exposure of 2,3-dimethyl-2-butene to photooxidation resulted in formation of the corresponding alkene hydroperoxide, namely 2,3-dimethyl-3-hydroperoxy-1-butene.

Exposure of propylene to photooxidation resulted in propylene oxide, acrolein and alloy hydroperoxide depending on the temperature of the zeolite matrix. Results are seen in FIGS. 9 and 10.

Thermal Oxidation

Thermal oxidation in darkness was performed as described in Example 3. Propylene submitted to thermal oxidation in dark was converted to allyl hydroperoxide and to propylene oxide.

What is claimed:

1. A process for selective conversion of a hydrocarbon to a partially oxygenated derivative of said hydrocarbon, said process comprising steps:

(a) selecting a zeolite matrix having an electrostatic field from about 0.15 V/Å to about 2.0 V/Å;

(b) absorbing a hydrocarbon of size of no more than 100 atoms and oxygen in gaseous phase onto the zeolite matrix; and (c) subjecting the zeolite matrix of step (b) to thermal oxidation in darkness conditions selectively converting the hydrocarbon into said oxygenated derivative with about 95% selectivity.

2. The process of claim 1, wherein the zeolite matrix is alkaline metal or alkaline earth element Y, L or pentasil zeolite.

3. The process of claim 2, wherein the zeolite matrix is NaY, BaY, CaY, NaL, KL, BaL, or CaY.

4. The process of claim 3 wherein the hydrocarbon is selected from the group consisting of a substituted or unsubstituted linear or branched alkane having from 1 to 20 carbon atoms, substituted or unsubstituted linear or branched alkene, aromatic and cycloalkyl having from 1 to 10 carbon atoms.

5. The process of claim 4 wherein the hydrocarbon is alkane selected from the group consisting of a substituted, unsubstituted, linear and branched methane, ethane, propane, isopropane, butane, tert-butane, pentane, hexane, heptane, octane, nonane, decane, isobutane, isopentane, and neopentane.

6. The process of claim 5 wherein the zeolite matrix of step (b) is subjected to thermal oxidation performed at temperatures from about 20° C. to about 150° C. for 30 minutes to 20 hours in darkness.

7. The process of claim 6 wherein the hydrocarbon is adsorbed onto the zeolite matrix in an amount from about 0.5 to about 5 molecules per one nanocage or per about 500 Å$^3$ of the zeolite matrix under pressure from about 1 to about 10 atm and at a temperature of about 50° C. to about 150° C.

8. The process of claim 4 wherein the hydrocarbon is alkene selected from the group consisting of substituted, unsubstituted, linear and branched ethylene, propylene, butene, pentene, hexene, heptene and octene.

9. The process of claim 8 wherein the zeolite matrix of step (b) is subjected to thermal oxidation performed at temperatures from about 20° C. to about 150° C. for 30 minutes to 20 hours in darkness.

10. The process of claim 9 wherein the hydrocarbon is adsorbed onto the zeolite matrix in an amount from about 0.5 to about 5 molecules per one nanocage or per about 500 Å$^3$ of the zeolite matrix under pressure from about 1 to about 10 atm and at a temperature of about 50° C. to about 150° C.

11. The process of claim 4 wherein the zeolite matrix of step (b) is subjected to thermal oxidation in darkness performed at temperatures from about 20° C. to about 150° C. for 30 minutes to 20 hours in darkness.

12. The process of claim 11 wherein the hydrocarbon is adsorbed onto the zeolite matrix in an amount from about 0.5 to about 5 molecules per one nanocage or per about 500 Å$^3$ of the zeolite matrix under pressure from about 1 to about 10 atm and at a temperature of about 50° C. to about 150° C.

13. The process of claim 3 wherein the zeolite matrix of step (b) is subjected to thermal oxidation performed at temperatures from about 20° C. to about 150° C. for 30 minutes to 20 hours in darkness.

14. The process of claim 13 wherein the hydrocarbon is adsorbed onto the zeolite matrix in an amount from about 0.5 to about 5 molecules per one nanocage or per about 500 Å$^3$ of the zeolite matrix under pressure from about 1 to about 10 atm and at a temperature of about 50° C. to about 150° C.

15. The process of claim 3 wherein the hydrocarbon is unsubstituted or alkyl substituted benzene, cumene, naphthalene, anthracene or toluene.

16. The process of claim 15 wherein the zeolite matrix of step (b) is subjected to thermal oxidation performed at temperatures from about 20° C. to about 150° C. for 30 minutes to 20 hours in darkness.

17. The process of claim 16 wherein the hydrocarbon is adsorbed onto the zeolite matrix in an amount from about 0.5 to about 5 molecules per one nanocage or per about 500 Å$^3$ of the zeolite matrix under pressure from about 1 to about 10 atm and at a temperature of about 50° C. to about 150° C.

18. The process of claim 3 wherein the hydrocarbon is unsubstituted or substituted cyclopropane, cyclobutane, cyclopentane, cyclohexane, cycloheptane or cyclooctane.

\* \* \* \* \*